(12) United States Patent
Huo

(10) Patent No.: US 7,553,556 B2
(45) Date of Patent: *Jun. 30, 2009

(54) ORGANOMETALLIC MATERIALS AND ELECTROLUMINESCENT DEVICES

(75) Inventor: Shouquan Huo, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 664 days.

This patent is subject to a terminal disclaimer.

(21) Appl. No.: 11/102,380

(22) Filed: Apr. 8, 2005

(65) Prior Publication Data

US 2006/0228579 A1    Oct. 12, 2006

(51) Int. Cl.
H01L 51/54 (2006.01)
(52) U.S. Cl. .............. 428/690; 428/917; 313/504; 313/506
(58) Field of Classification Search ......... 428/690, 428/917; 313/504, 506; 257/E51.044; 546/4, 546/6, 10; 548/103, 402; 556/13
See application file for complete search history.

(56) References Cited

U.S. PATENT DOCUMENTS

| 6,284,895 | B1  | 9/2001  | Thanki et al. |
| 6,670,772 | B1* | 12/2003 | Arnold et al. ............ 315/169.3 |
| 6,824,895 | B1* | 11/2004 | Sowinski et al. ............ 428/690 |
| 7,029,766 | B2* | 4/2006  | Huo et al. ..................... 428/690 |
| 2002/0179885 | A1* | 12/2002 | Che et al. .............. 252/301.16 |
| 2006/0094875 | A1* | 5/2006  | Itoh et al. ...................... 546/2 |

FOREIGN PATENT DOCUMENTS

WO    WO 2004/039781    *    5/2004

OTHER PUBLICATIONS

Albert et al., Organometallics, (1995), vol. 14, p. 1393-1404.*
Bohm et al., Journal of Organometallic Chemistry, vol. 588, (1999), p. 247-255.*
Yoneda et al., Organometallics, (1994), vol. 13, p. 4912-4918.*
Sanna et al., Inorganic Chimica Acta, 305, (2000), p. 189-205.*
W. Lu, et al., ππ Interactions in Organometallic Systems. Crystal Structures and Spectroscopic Properties of Luminescent Mono-, Bi-, and Trinuclear Trans-cyclometalated Platinum (II) Complexes Derived from 2,6-Diphenylpyridine, Organometallics, 2001, 20, pp. 2477-2486.
S. Huo, et al., "Organic Element for Electroluminescent Devices", U.S. Appl. No. 10/729,238, filed Dec. 5, 2003.

* cited by examiner

Primary Examiner—Dawn Garrett
(74) Attorney, Agent, or Firm—Arthur E. Kluegel; Raymond L. Owens

(57) ABSTRACT

An electroluminescent device comprises a light-emitting layer containing a light emitting material that contains an organometallic complex having a partial structure represented by the following formula (I):

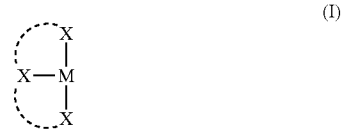

wherein,
  M represents a metal selected from group 8, 9, or 10 metals; and
  one X is a carbon that forms a covalent bond with M and the other two X is are heteroatoms, one of which forms a coordinative bond with M and the other of which forms a covalent bond with M;
  wherein all of the Xs are linked together to form a dianionic tridentate cyclometallating ligand to form a five or six-membered metallocycle with M where each X can be a part of a separate cyclic or acyclic structure.

8 Claims, 3 Drawing Sheets

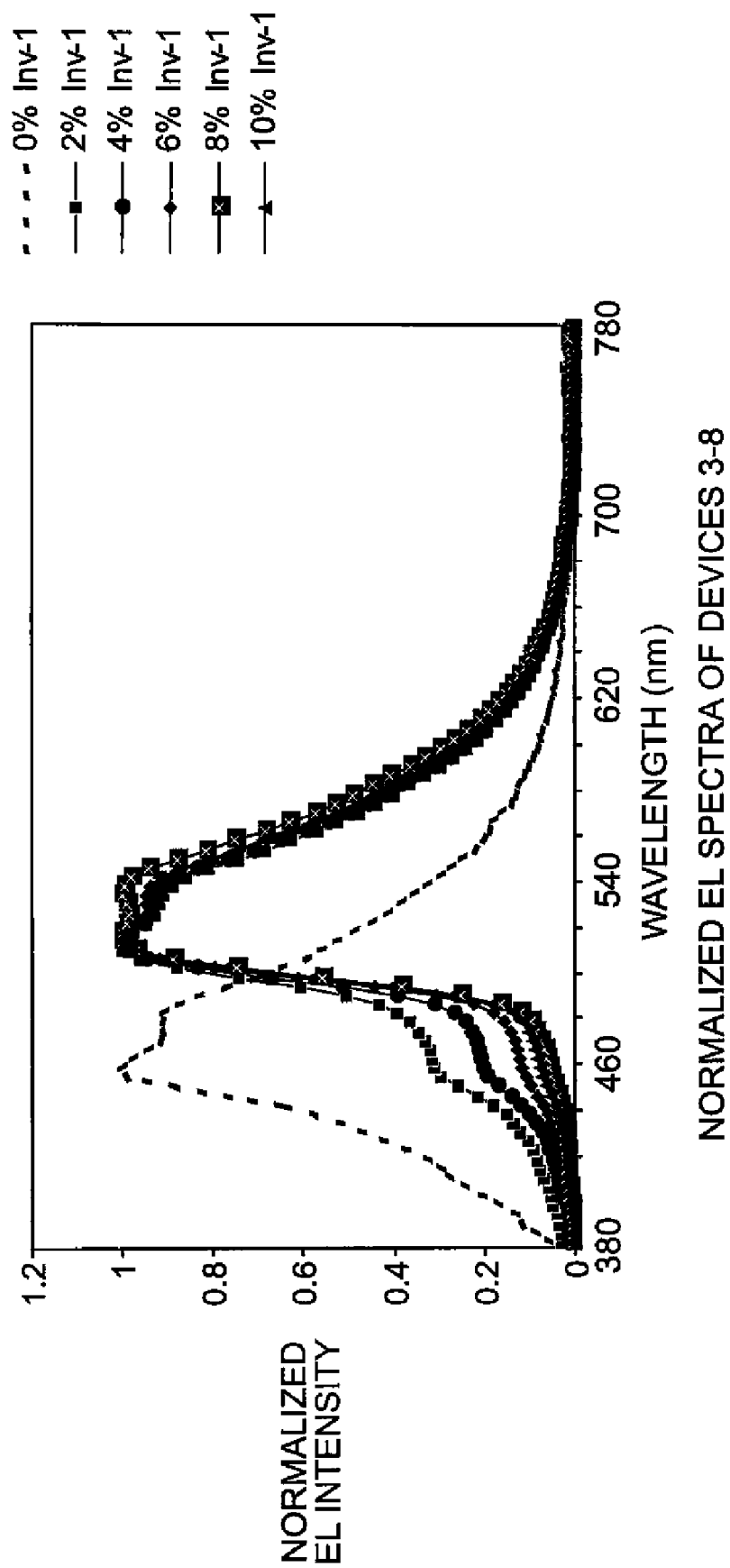

ORGANOMETALLIC MATERIALS AND ELECTROLUMINESCENT DEVICES

FIELD OF THE INVENTION

This invention relates to an organic light emitting diode (OLED) electroluminescent (EL) device comprising a light-emitting layer containing a certain organometallic complex that provides desirable electroluminescent properties. The invention also relates to a new organometallic complex.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 µm). Consequently, operating voltages were very high, often >100V.

More recent organic EL devices include an organic EL element consisting of extremely thin layers (e.g. <1.0 µm) between the anode and the cathode. Herein, the term "organic EL element" encompasses the layers between the anode and cathode electrodes. Reducing the thickness lowered the resistance of the organic layer and has enabled devices that operate at much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, Vol. 65, Pages 3610-3616, 1989]. The light-emitting layer commonly consists of a host material doped with a guest material. Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

Many emitting materials that have been described as useful in an OLED device emit light from their excited singlet state by fluorescence. The excited singlet state is created when excitons formed in an OLED device transfer their energy to the excited state of the dopant. However, it is generally believed that only 25% of the excitons created in an EL device are singlet excitons. The remaining excitons are triplet, which cannot readily transfer their energy to the singlet excited state of a dopant. This results in a large loss in efficiency since 75% of the excitons are not used in the light emission process.

Triplet excitons can transfer their energy to a dopant if it has a triplet excited state that is low enough in energy. If the triplet state of the dopant is emissive it can produce light by phosphorescence. In many cases singlet excitons can also transfer their energy to lowest singlet excited state of the same dopant. The singlet excited state can often relax, by an inter-system crossing process, to the emissive triplet excited state. Thus, it is possible, by the proper choice of host and dopant, to collect energy from both the singlet and triplet excitons created in an OLED device and to produce a very efficient phosphorescent emission.

One class of useful phosphorescent materials are cyclometallated transition metal complexes having a triplet excited state. For example, fac-tris(2-phenylpyridinato-N,$C^{2'}$)iridium(III) (Ir(ppy)$_3$) strongly emits green light from a triplet excited state owing to the large spin-orbit coupling of the heavy atom and to the lowest excited state which is a charge transfer state having a Laporte allowed (orbital symmetry) transition to the ground state (K. A. King, P. J. Spellane, and R. J. Watts, *J. Am. Chem. Soc.*, 107, 1431 (1985), M. G. Colombo, T. C. Brunold, T. Reidener, H. U. Gudel, M. Fortsch, and H.-B. Burgi, *Inorg. Chem.*, 33, 545 (1994). Small-molecule, vacuum-deposited OLEDs having high efficiency have also been demonstrated with Ir(ppy)$_3$ as the phosphorescent material and 4,4'-N,N'-dicarbazole-biphenyl (CBP) as the host (M. A. Baldo, S. Lamansky, P. E. Burrows, M. E. Thompson, S. R. Forrest, *Appl. Phys. Lett.*, 75, 4 (1999), T. Tsutsui, M.-J. Yang, M. Yahiro, K. Nakamura, T. Watanabe, T. Tsuji, Y. Fukuda, T. Wakimoto, S. Miyaguchi, *Jpn. J. Appl. Phys.*, 38, L1502 (1999)).

Another class of phosphorescent materials include compounds having interactions between atoms having $d^{10}$ electron configuration, such as Au$_2$(dppm)Cl$_2$ (dppm=bis(diphenylphosphino)methane) (Y. Ma et al, *Appl. Phys. Lett.*, 74, 1361 (1998)). Still other examples of useful phosphorescent materials include coordination complexes of the trivalent lanthanides such as Tb$^{3+}$ and Eu$^{3+}$ (J. Kido et al, *Appl. Phys. Lett.*, 65, 2124 (1994)). While these latter phosphorescent compounds do not necessarily have triplets as the lowest excited states, their optical transitions do involve a change in spin state of 1 and thereby can harvest the triplet excitons in OLED devices.

Although many phosphorescent cyclometallated Ir complexes have been described as useful in an EL device, Pt-based organometallic complexes have not been examined as extensively. Some Pt phosphorescent complexes include cyclometallated Pt(II) complexes such as cis-bis(2-phenylpyridinato-N,$C^{2'}$)platinum(II), cis-bis(2-(2'-thienyl)pyridinato-N,$C^{3'}$)platinum(II), cis-bis(2-(2'-thienyl)quinolinato-N,$C^{5'}$)platinum(II), or (2-(4,6-diflourophenyl)pyridinato-NC2')platinum(II)acetylacetonate. However, those complexes do not give high efficiency or stability. Further, some of those complexes are not stable toward sublimation (S. Lamansky et al., WO 00/57676) and thus not suitable for vacuum-deposition to form organic films. Pt(II) porphyrin complexes such as 2,3,7,8,12,13,17,18-octaethyl-21H, 23H-porphine platinum (II) are reported in U.S. Pat. No. 6,048,630 as useful phosphorescent materials in an electroluminescent device although they did not give a very high luminance yield. Recently, C. Che, W. Lu, and M. Chan reported organometallic light-emitting materials based on (C^N^N) tridentate cyclometalated Pt(II) arylacetylides. (US 2002/0179885 and references cited therein). We have also disclosed organometallic light-emitting materials based on (C^N^N) tridentate cyclometallated Pt(II) complexes (U.S. Pat. No. 6,824,895

B1) and (N^C^N) tridentate cyclometallated Pt(II) complexes that have been disclosed in prior filing Ser. No. 10/729,238 filed on Dec. 15, 2003. Furthermore, the coordinatively unsaturated square planar Pt(II) complexes tend to aggregate at high concentration, leading to concentration quenching or the formation of eximers that can affect the hue of OLED devices made of them.

Further, Wei Lu et al reported tridentate cyclometallated Pt(II) complexes based on 2,6-diphenylpyridine (Wei Lu, Michael C. W. Chan, Kung-Kai Cheung, and Chi-Ming Che, Organometallics 2001, 20, 2477-2486). Although the complexes are photoluminescent in the solid state and in 77 K methanol/ethanol glass, no emission is detected in dichloromethane at room temperature. Therefore, the complexes do not appear to be highly efficient emitters useful in electroluminescent devices.

It is a problem to be solved to provide new organometallic materials that will function as phosphorescent materials in an electroluminescent device having improved luminance and luminescence efficiency.

SUMMARY OF THE INVENTION

The invention provides an electroluminescent device comprising a light-emitting layer containing a light emitting material that comprises an organometallic complex having a partial structure represented by the following formula (I):

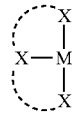

(I)

wherein,

M represents a metal selected from group 8, 9, or 10 metals; and one X is a carbon that forms a covalent bond with M and the other two Xs are heteroatoms, one of which forms a coordinative bond with M and the other of which forms a covalent bond with M;

wherein all of the Xs are linked together to form a dianionic tridentate cyclometallating ligand to form a five or six-membered metallocycle with M where each X can be a part of a separate cyclic or acyclic structure.

The invention also relates to an organometallic complex.

The device exhibits improved luminance and luminescence efficiency.

BRIEF DESCRIPTION OF THE DRAWINGS

FIG. 3 shows the normalized electroluminescent intensity of devices 3, 4, 5, 6, and 7 with phosphorescent organometallic dopant (Inv-1) level of 2%, 4%, 6%, 8%, and 10% respectively in the visible spectrum as a function of wavelength at the current density of 20 mA/cm². Also shown is the normalized electroluminescent intensity of undoped comparative device 8 (dashed line) in the visible spectrum as a function of wavelength at the current density of 20 mA/cm².

DETAILED DESCRIPTION OF THE INVENTION

Figure 1:
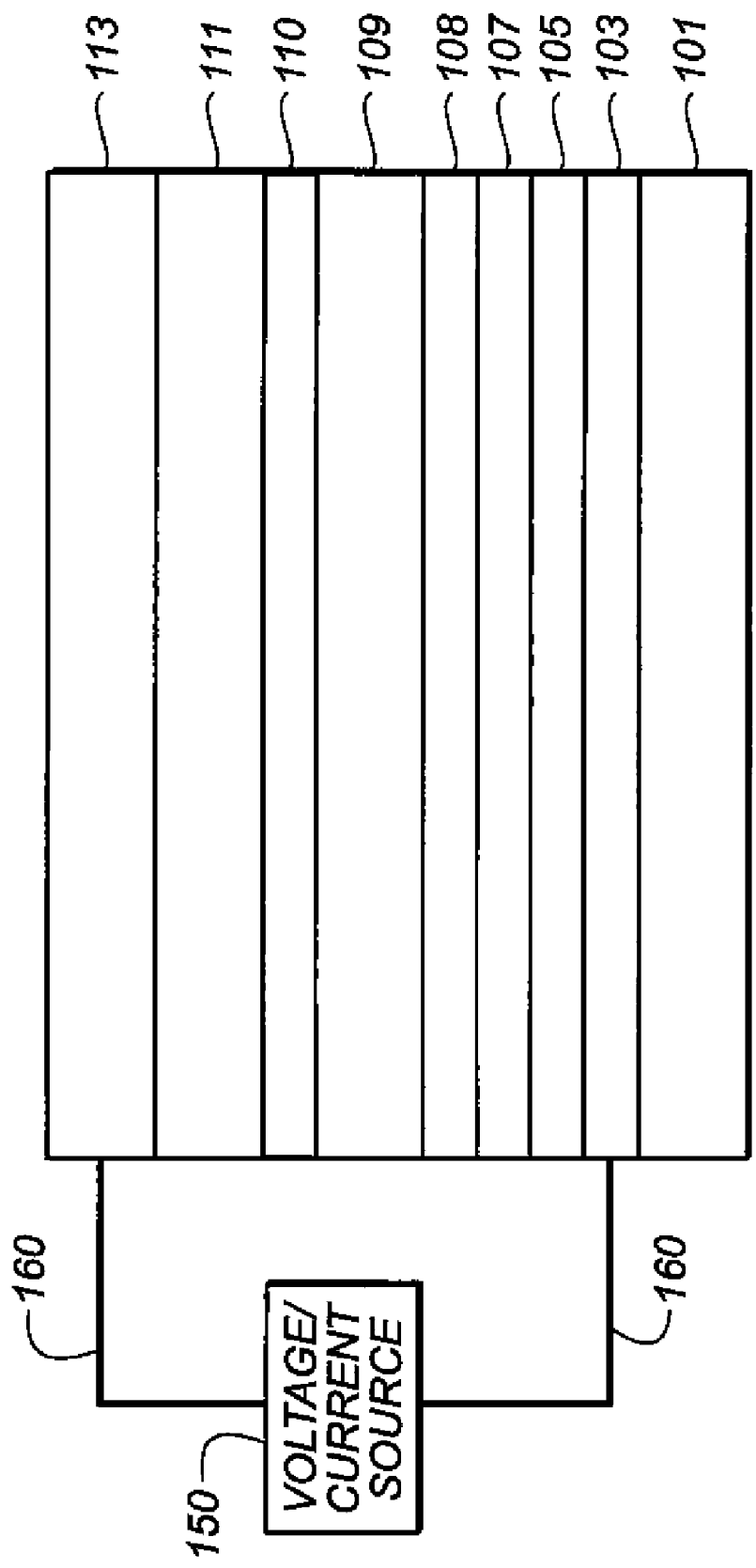
FIG. 1 shows a schematic cross-section of a typical OLED device in which this invention can be used. Since device feature dimensions such as layer thicknesses are frequently in sub-micrometer ranges, the drawings are scaled for ease of visualization rather than dimensional accuracy.

The invention is summarized above. In one suitable embodiment, the tridentate organometallic complex can be incorporated into a polymer light emitting diode (PLED) device. For example, the organometallic complex can be part of the main chain of a polymer, the side chain, or intermixed with a polymer in such a device.

Suitably, the organometallic complex of the invention can be represented by the formula (II)-(VI);

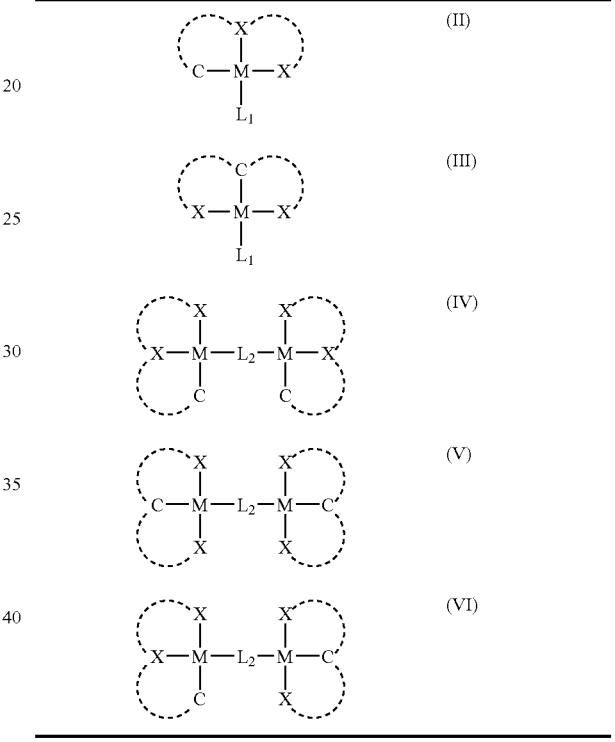

Wherein,

M represents a metal selected from group 10, desirably Pt.

C represents a carbon atom. Desirably, C is an sp² carbon, more desirably a carbon of an aromatic ring.

X represents a heteroatom selected from N, P, O, and S. One X forms a covalent bond with the metal. The other X forms a coordinative bond with the metal.

C and X are linked together to form a dianionic tridentate cyclometallating ligand represented by LH₂ which forms an cyclometallated transition metal complex represented by ML by losing two protons. Illustrative examples of suitable tridentate ligands useful in this invention are shown below.

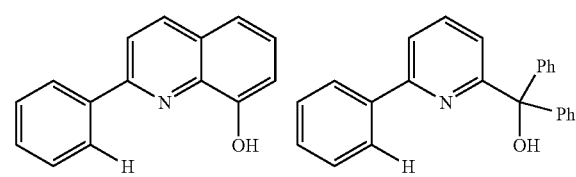

-continued

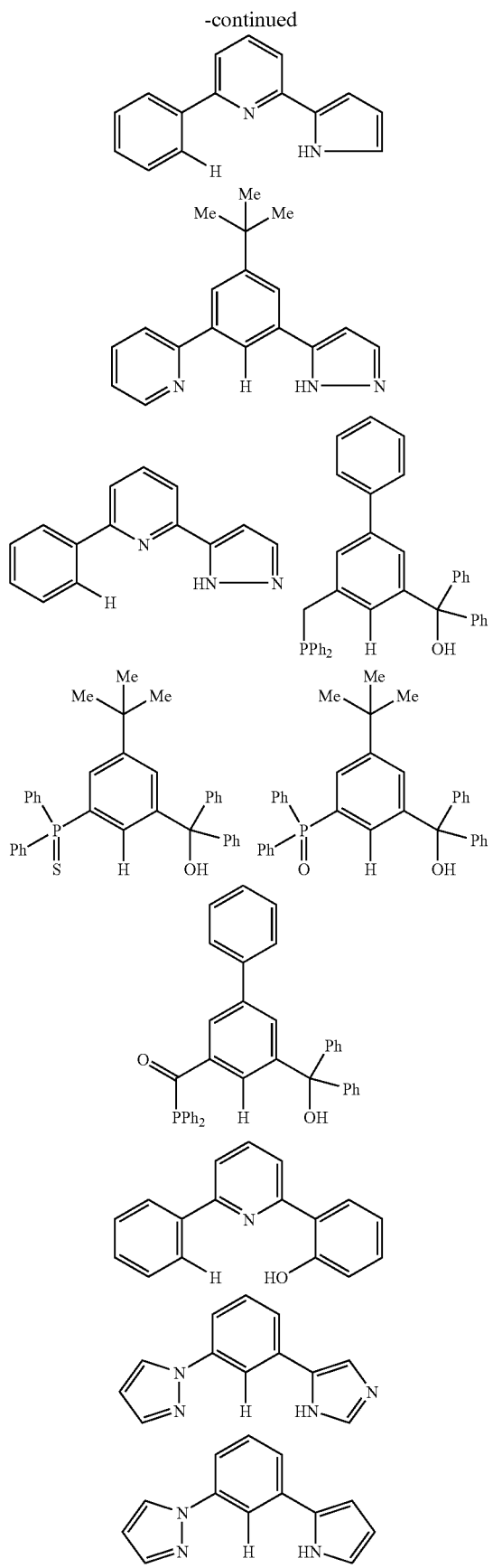

-continued

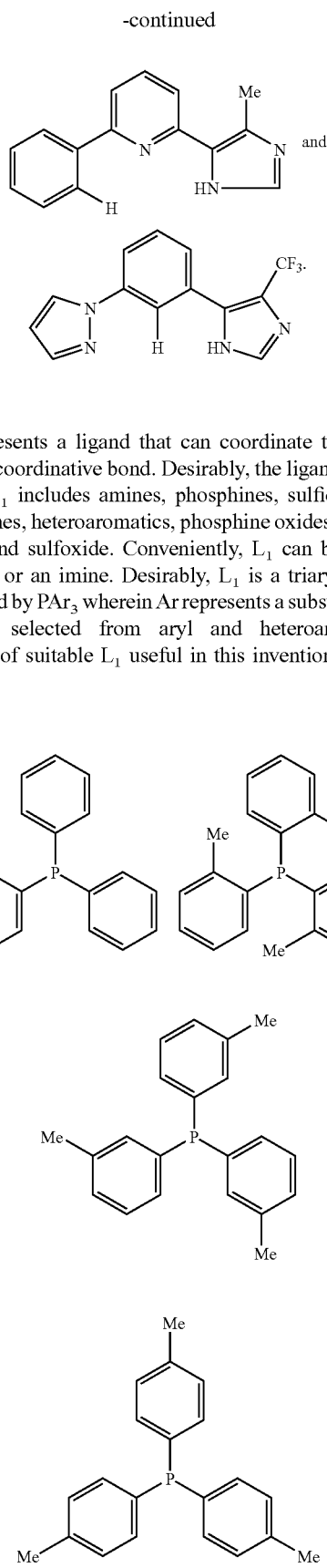

$L_1$ represents a ligand that can coordinate to the metal through a coordinative bond. Desirably, the ligand is neutral. Suitable $L_1$ includes amines, phosphines, sulfides, isocyanides, imines, heteroaromatics, phosphine oxides, phosphine sulfides, and sulfoxide. Conveniently, $L_1$ can be a tertiary phosphine or an imine. Desirably, $L_1$ is a triarylphosphine represented by $PAr_3$ wherein Ar represents a substituent independently selected from aryl and heteroaryl groups. Examples of suitable $L_1$ useful in this invention are shown below.

-continued
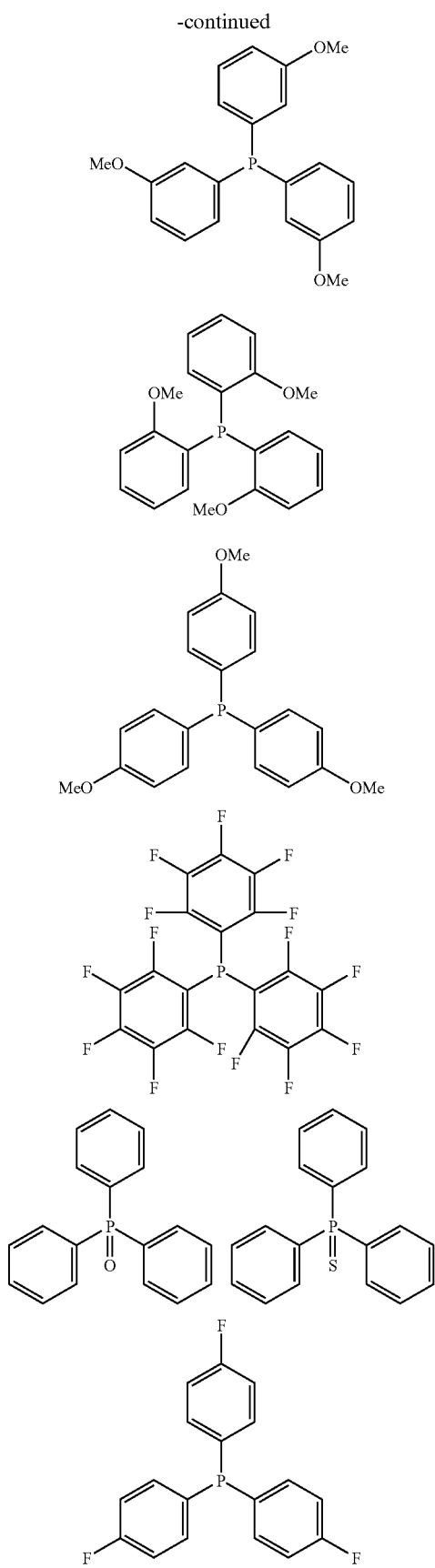
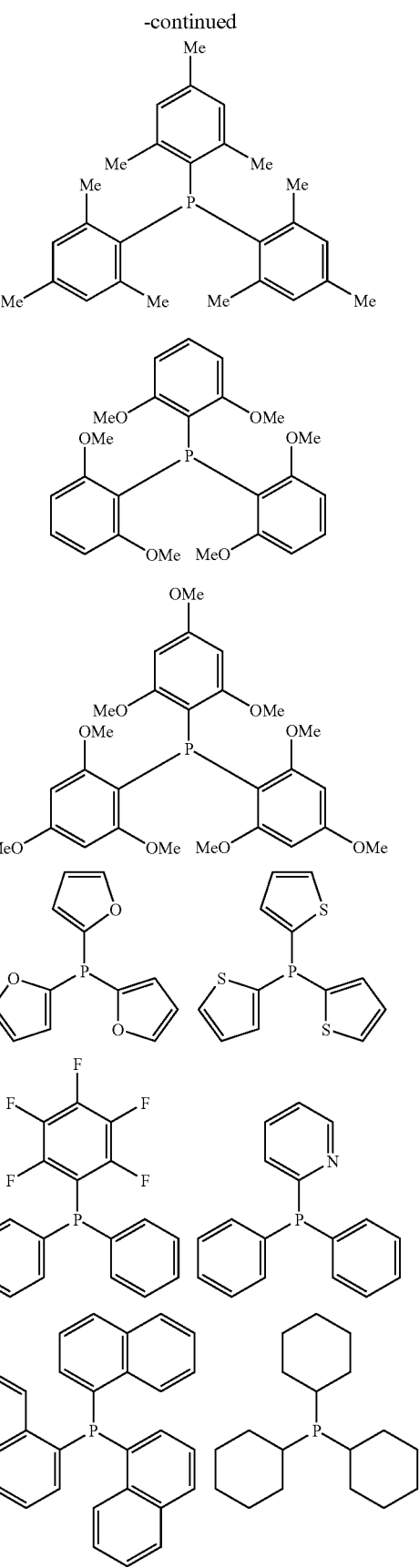

-continued

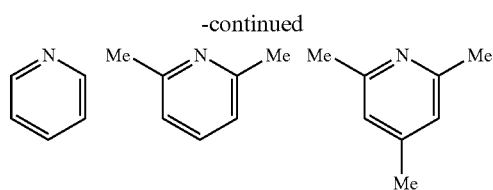

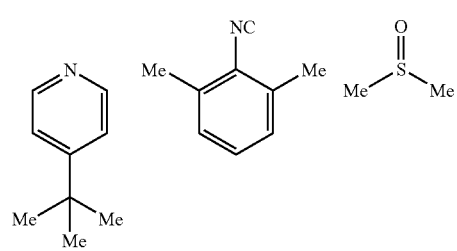

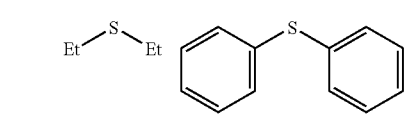

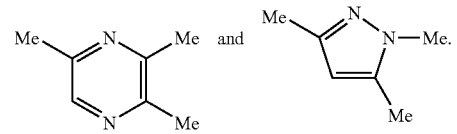

L₂ represents a ligand that contains at least two donors that can coordinate to two metals through two coordinative bonds. Desirably the ligand is a neutral ligand containing at least two donors selected from N, P, O, and S. Examples of suitable $L_2$ are shown below.

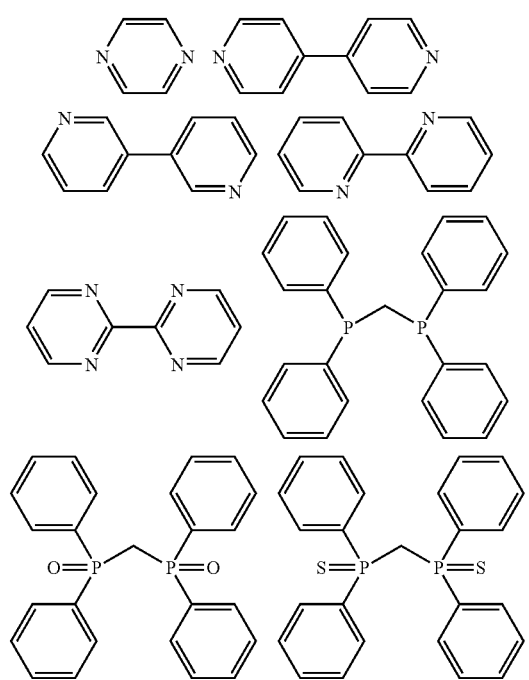

-continued

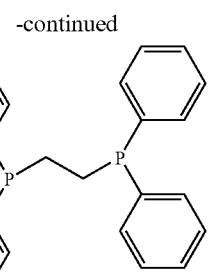

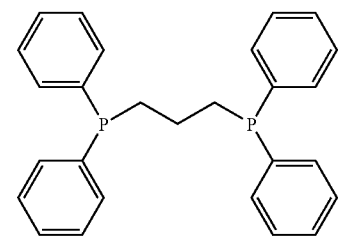

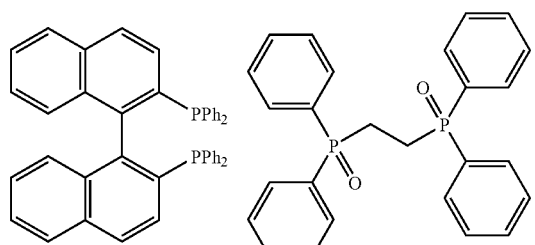

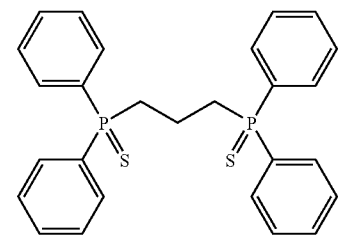

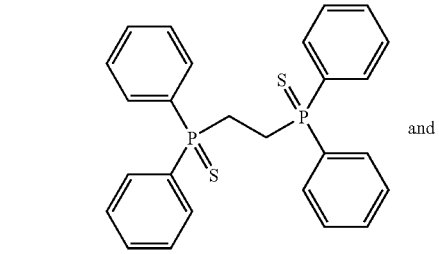

and

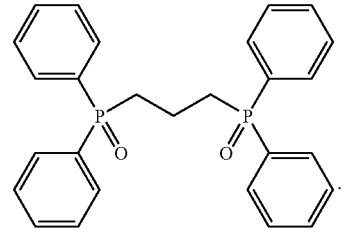

In one desirable embodiment, the organometallic complex of the invention can be represented by Formula (VII) and (VIII):

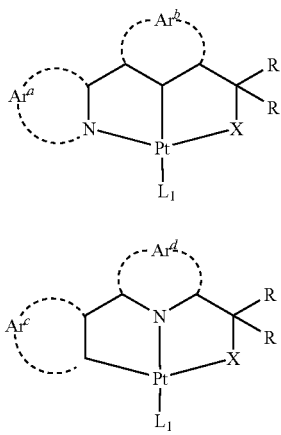

wherein,

Ar$^a$, Ar$^b$, Ar$^c$, and Ar$^d$ independently represent the atoms necessary to form a five or six-membered aromatic ring, which may be further substituted including substitution by fused rings. The term 'aromatic rings' includes aromatic rings that have heteroatoms present in the ring, see for example, J. March, *Advanced Organic Chemistry*, Chapter 2 (1985, publisher John Wiley & Sons, New York, N.Y.). For example, Ar$^b$ and Ar$^c$ can represent the atoms necessary to form groups such as benzene ring groups, thiophene ring groups, or furan ring groups. Likewise, Ar$^a$ and Ar$^d$ can represent the atoms necessary to form groups such as pyridine ring groups, quinoline ring groups, isoquinoline ring groups, and indole ring groups as examples. In one desirable embodiment, Ar$^b$ and Ar$^c$ represents a benzene ring group and Ar$^a$ and Ar$^d$ independently represent pyridine ring groups.

R represents independently selected substituent group, provided that two Rs can combine to form a ring.

X represents O or S.

L$_1$ represents a ligand selected from amines, phosphines, imines, sulfides, isocynides, heteroaromatics, phosphine oxides, phosphine sulfides, and sulfoxides. Suitable ligand L$_1$ has been listed above.

In another desirable embodiment, the organometallic complex of the invention can be represented by the following formula (IX):

(IX)

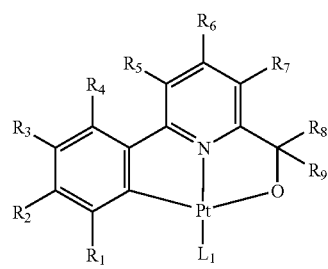

wherein

R$^1$-R$^9$ represent hydrogen or independently selected substituent groups, provided that R$^1$ and R$^2$, R$^2$ and R$^3$, R$^3$ and R$^4$, R$^4$ and R$^5$, R$^5$ and R$^6$, R$^6$ and R$^7$, R$^7$ and R$^8$, as well as R$^8$ and R$^9$ may combine to form a ring group; desirably, R$^8$ and R$^9$ represent non-hydrogen groups such as alkyl and aryl groups.

L$_1$ represents a liagnd that coordinate to the Pt through a coordinative bond. Suitable ligand L$_1$ have been listed above.

In another suitable embodiment, the organometallic complex of the invention can be represented by the formula (X):

(X)

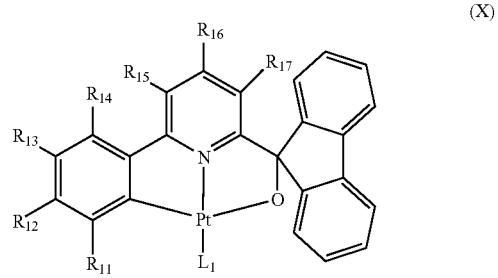

wherein,

R$^{11}$-R$^{17}$ represent hydrogen or independently selected substituent groups, provided that adjacent two groups may combine to form a ring group, as well as R$^{14}$ and R$^{15}$ may combine to form a ring group.

L$_1$ represents a liagnd that can coordinate to the Pt through a coordinative bond. Suitable L$_1$ have been listed above.

Synthesis of the emitting materials useful in the invention may be accomplished by preparing an organic ligand and then using a metal to complex with the ligand and form the organometallic complex. For example, suitable dianionic tridentate cyclometallating ligands can be prepared by the method outlined in Scheme 1. The first step involves a Pd-catalyzed cross coupling of an aryl metal and a dibromoarene, which give the mono-substituted precursor. The precursor undergoes Li—Br exchange then nucleophilic addition to a ketone to form a dianionic tridentate cyclometallating ligand.

Scheme 1

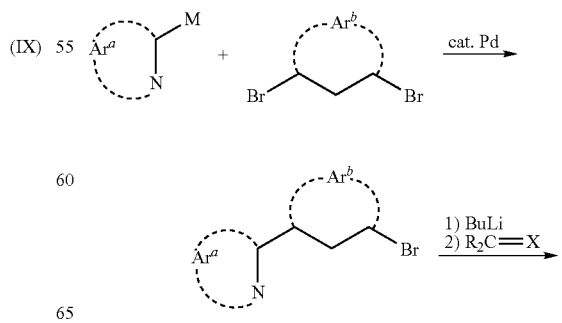

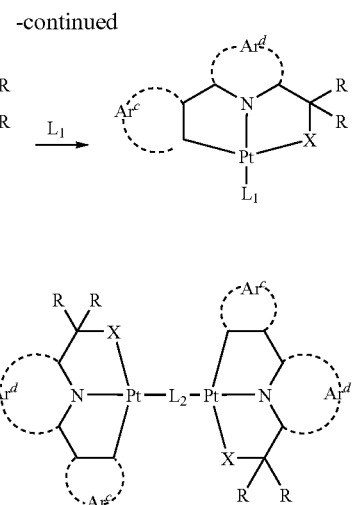

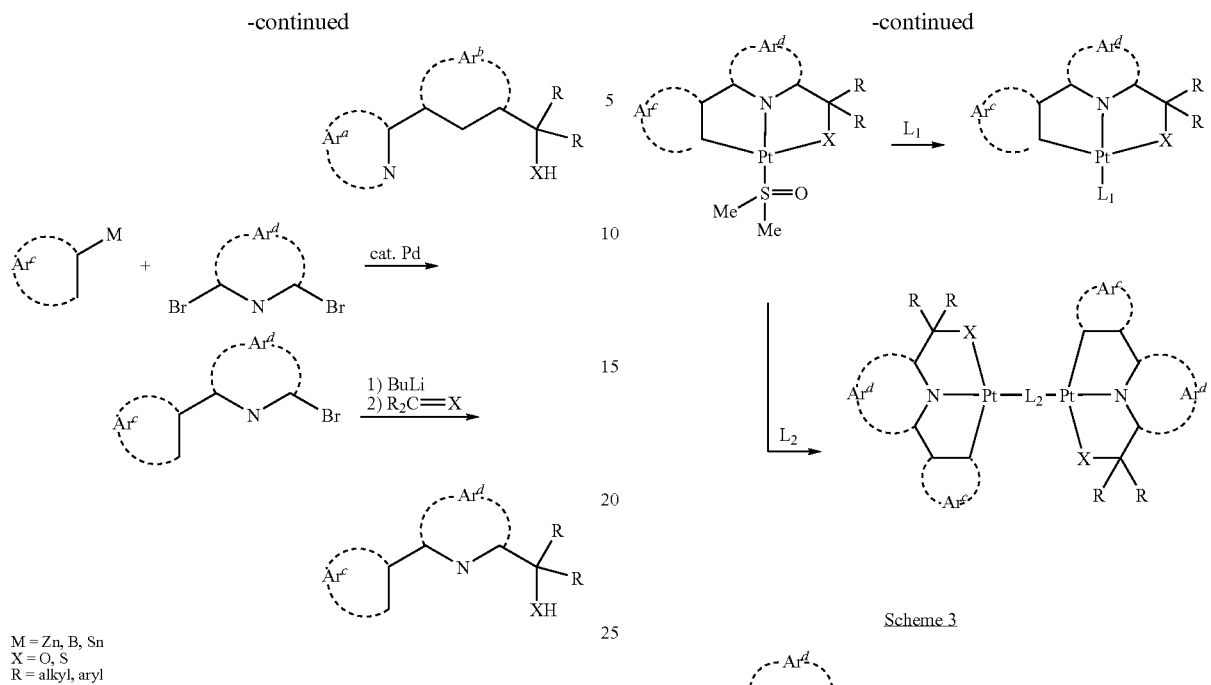

M = Zn, B, Sn
X = O, S
R = alkyl, aryl

In Scheme 2 is shown a general formation of the organometallic complex by reacting the tridentate ligand prepared above with $K_2PtCl_4$ in acetic acid. The product obtained from the reaction is treated with DMSO to give a DMSO complex. The DMSO in the complex can be replaced by other mono or bidentate ligands to form suitable organometallic complexes. Alternatively, the suitable complexes can be prepared by reacting the tridentate cyclometallating ligand with $Pt(DMSO)_2Cl_2$ to give DMSO complex followed by the ligand exchange with other mono- or bidentate ligand as shown in Scheme 3.

Scheme 2

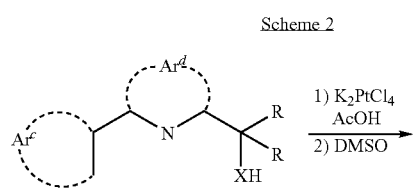

Scheme 3

Illustrative examples of complexes of Formula 1-10 useful in the present invention are but not limited to the following:

Inv-1

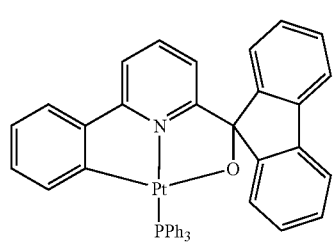

Inv-2

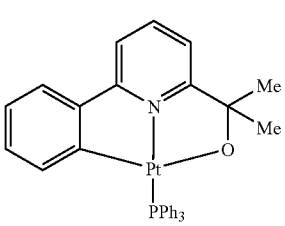

-continued
Inv-3
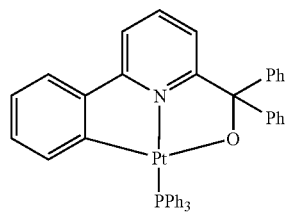
Inv-4
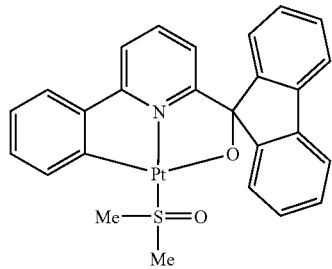
Inv-5
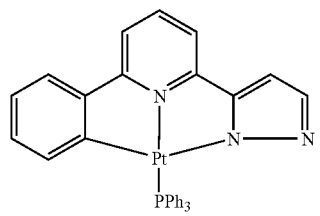
Inv-6
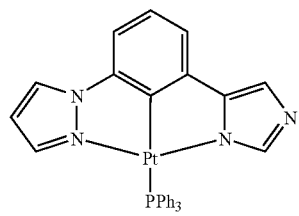
Inv-7
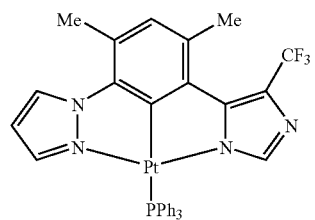
Inv-8
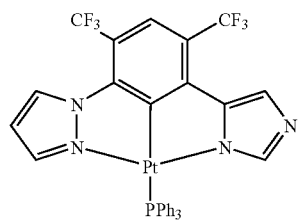
Inv-9
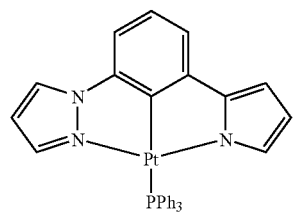
Inv-10
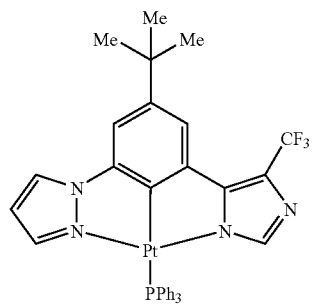
Inv-11
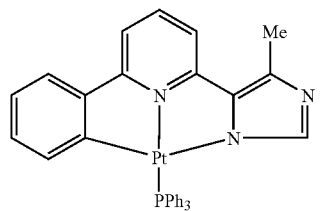
Inv-12
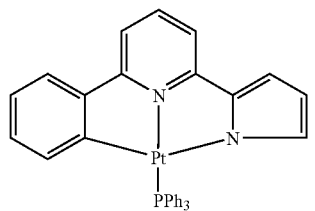
Inv-13
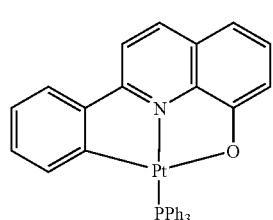
Inv-14
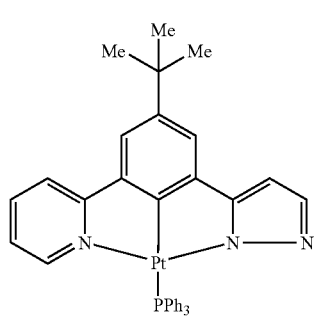

-continued
Inv-15
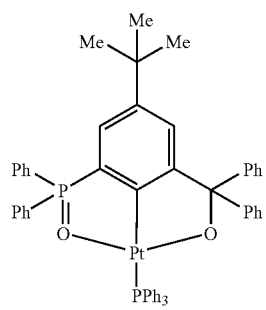
Inv-16
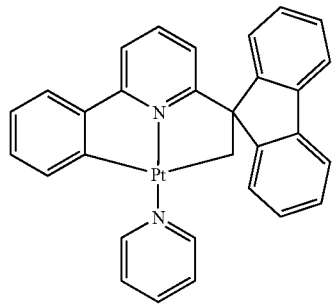
Inv-17
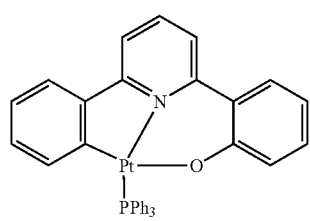
Inv-18
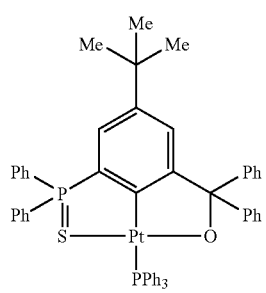
Inv-19
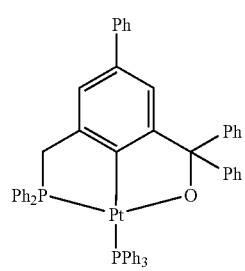
Inv-20
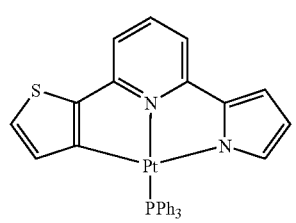
Inv-21
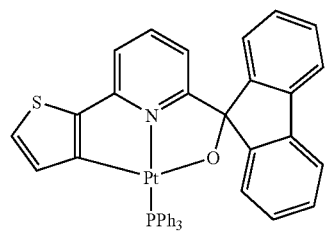
Inv-22
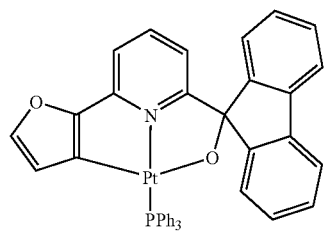
Inv-23
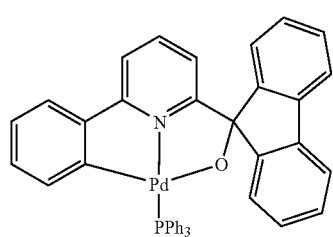
Inv-24
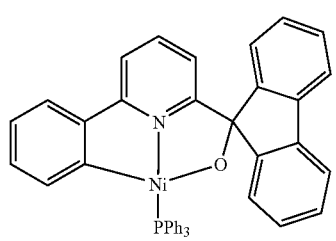

-continued
Inv-25
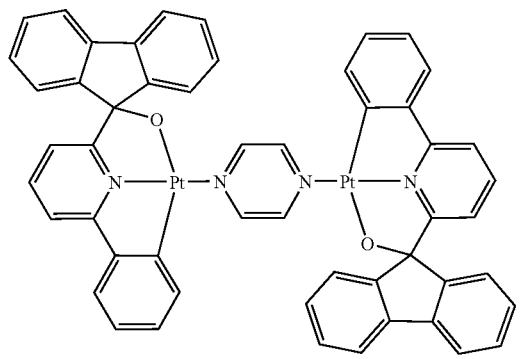
Inv-26
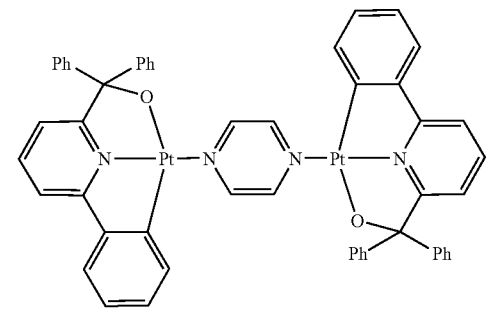
Inv-27
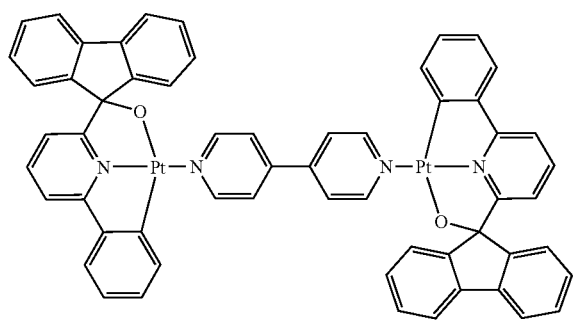
Inv-28
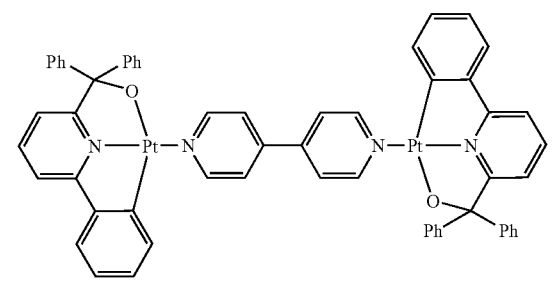
Inv-29
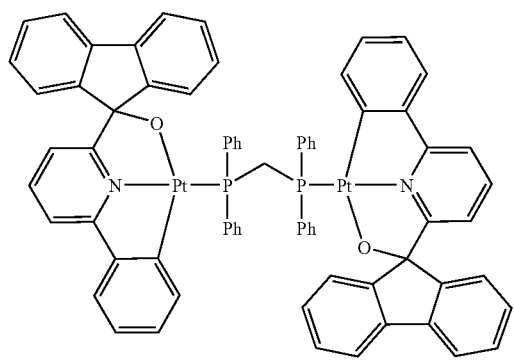
Inv-30
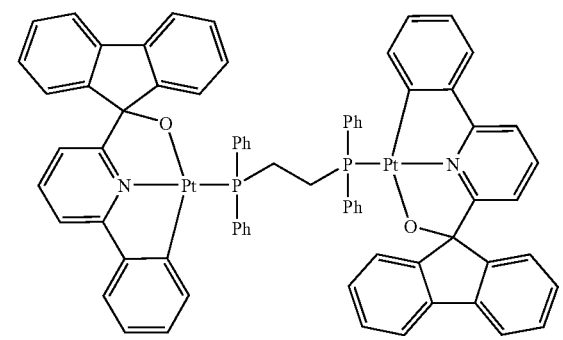
Inv-31
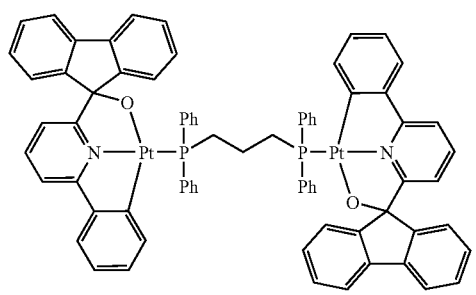
Inv-32
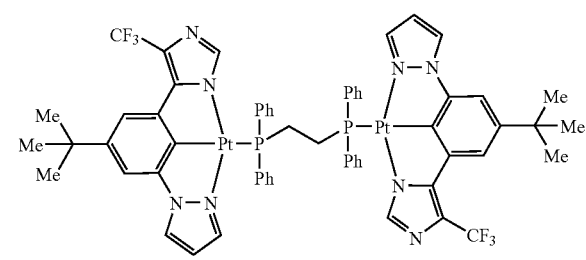

-continued

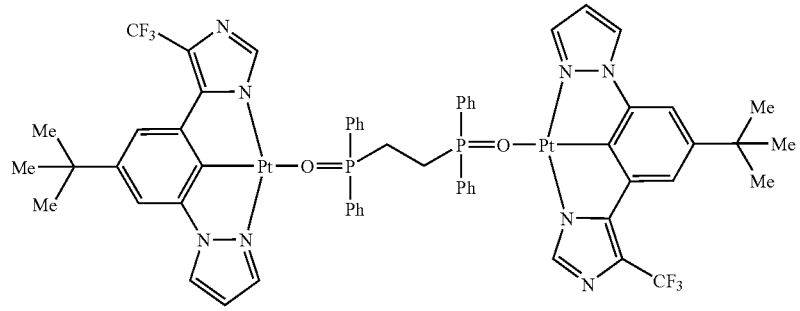

Inv-33

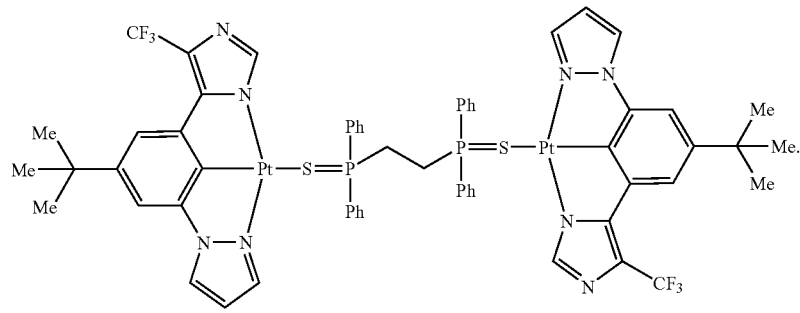

Inv-34

Embodiments of the invention may provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

The organometallic complexes may be useful in other applications than electroluminescent devices. For example, the complexes may be useful in catalysis or may be used as oxygen sensors and biosensors and the like.

Unless otherwise specifically stated, use of the term "substituted" or "substituent" means any group or atom other than hydrogen. Unless otherwise specifically stated, use of the term "aromatic ring system" means a system of one ring or more than one ring fused together, where the entire ring system is aromatic. Unless otherwise specifically stated, use of the term "substituted phenyl ring" means a phenyl ring that is substituted and may be substituted to form one substituted or unsubstituted fused aromatic ring system, or more than one substituted or unsubstituted fused aromatic ring systems. Unless otherwise provided, when a group (including a compound or complex) containing a substitutable hydrogen is referred to, it is also intended to encompass not only the unsubstituted form, but also form further substituted with any substituent group, or groups as herein mentioned, including a fused ring, so long as the substituent does not destroy properties necessary for utility. Suitably, a substituent group may be halogen or may be bonded to the remainder of the molecule by an atom of carbon, silicon, oxygen, or phosphorous. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. such as pyridyl, thienyl, furyl, azolyl, thiazolyl, oxazolyl, imidazolyl, pyrazolyl, pyrazinyl, pyrimidinyl, pyrolidinonyl, quinolinyl, isoquinolinyl, 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups.

General Device Architecture

The present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light-emitting layer located between the anode and cathode. Additional layers may be employed as more fully described hereafter.

A typical structure, especially useful for of a small molecule device, is shown in FIG. 1 and is comprised of a substrate 101, an anode 103, a hole-injecting layer 105, a hole-transporting layer 107, an exciton blocking layer 108, a light-emitting layer 109, a hole- or exciton-blocking layer 110, an electron-transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

The anode and cathode of the OLED are connected to a voltage/current source 150 through electrical conductors 160. The OLED is operated by applying a potential between the anode and cathode such that the anode is at a more positive potential than the cathode. Holes are injected into the organic EL element from the anode and electrons are injected into the organic EL element at the cathode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate where either the cathode or anode can be in contact with the substrate. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. For applications where the EL emission is viewed through the top electrode, the transmissive characteristic of the bottom support can be light transmissive, light absorbing or light reflective. Substrates for use in this case include, but are not limited to, glass, plastic, semiconductor materials, silicon, ceramics, and circuit board materials. Of course it is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Hole-Injecting Layer (HIL)

While not always necessary, it is often useful to provide a hole-injecting layer between the anode and the hole-transporting layer. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. Nos. 6,127, 004, 6,208,075 and 6,208,077, some aromatic amines, for example, m-MTDATA (4,4',4"-tris[(3-methylphenyl)phenylamino]triphenylamine), and inorganic oxides including vanadium oxide (VOx), molybdenum oxide (MoOx), and nickel oxide (NiOx). Alternative hole-injecting materials reportedly useful in organic EL devices are described in EP 0 891 121 A1 and EP 1 029 909 A1.

Hole-Transporting Layer (HTL)

The hole-transporting layer 107 contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. The hole-transporting layer can be formed of a single or a mixture of aromatic tertiary amine compounds. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
N,N,N',N'-tetraphenyl-4,4'''-diamino-1,1':4',1":4",1'''-quaterphenyl
Bis(4-dimethylamino-2-methylphenyl)phenylmethane
1,4-bis[2-[4-[N,N-di(p-toly)amino]phenyl]vinyl]benzene (BDTAPVB)
N,N,N',N'-Tetra-p-tolyl-4,4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl (NPB)
4,4'-Bis[N-(1-naphthyl)-N-(2-naphthyl)amino]biphenyl (TNB)
4,4'-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4'-Bis[N-(1-anthryl)-N-phenylamino]-p-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-p-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-p-terphenyl
4,4'-Bis{N-phenyl-N-[4-(1-naphthyl)-phenyl]amino}biphenyl
2,6-Bis[N,N-di(2-naphthyl)amino]fluorene
4,4',4"-tris[(3-methylphenyl)phenylamino]triphenylamine (MTDATA)
4,4'-Bis[N-(3-methylphenyl)-N-phenylamino]biphenyl (TPD) Another class of useful hole-transporting materials includes polycyclic aromatic compounds as described in EP 1 009 041. Some hole-injecting materials described in EP 0 891 121 A1 and EP 1 029 909 A1, can also make useful hole-transporting materials. In addition, polymeric hole-transporting materials can be used including poly(N-vinylcarbazole) (PVK), polythiophenes, polypyrrole, polyaniline, and copolymers including poly(3,4-ethylenedioxythiophene)/poly(4-styrenesulfonate) also called PEDOT/PSS.

Host Materials for Phosphorescent Materials

Suitable host materials should be selected so that the triplet exciton can be transferred efficiently from the host material to the phosphorescent material. For this transfer to occur, it is a highly desirable condition that the excited state energy of the phosphorescent material be lower than the difference in energy between the lowest triplet state and the ground state of the host. However, the band gap of the host should not be chosen so large as to cause an unacceptable increase in the drive voltage of the OLED. Suitable host materials are described in WO 00/70655; WO 01/39234; WO 01/93642; WO 02/074015; WO 02/15645, and US 20020117662. Suitable hosts include certain aryl amines, triazoles, metal-chelated oxinoid compounds, indoles and carbazole compounds. Examples of desirable hosts are bis(8-quinolinolato)(4-phenylphenolato)aluminum (III) (BAlQ-7), bis(8-quinolinolato) (2,6-diphenylphenolato)aluminum (III) (BAlQ-13), 4,4'-N,N'-dicarbazole-biphenyl (CBP), 2,2'-dimethyl-4,4'-N,N'-dicarbazole-biphenyl, m-(N,N'-dicarbazole)benzene, and poly(N-vinylcarbazole), including their derivatives.

Desirable host materials are capable of forming a continuous film.

The light emitting layer may contain more than one host material in order to improve the device's film morphology, electrical properties, light emission efficiency, and lifetime. In a preferred embodiment of the present invention, the light emitting layer contains a first co-host material that has good hole transporting properties, and a second co-host material that has good electron transporting properties.

The desirable hole transporting co-host may be any suitable hole transporting compound, such as a triarylamine or a carbazole, as long it has a triplet energy higher than that of the phosphorescent emitter to be employed.

A suitable class of hole transporting compounds for use as a co-host of the present invention are aromatic tertiary amines, by which it is understood to be compounds containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. in U.S. Pat. No. 3,180,730. Other suitable triarylamines substituted with one or more vinyl radicals and/or comprising at least one active hydrogen containing group are disclosed by Brantley et al. in U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural formula (A):

(A)

wherein $Q_1$ and $Q_2$ are independently selected aromatic tertiary amine moieties, and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

(B)

wherein $R_1$ and $R_2$ each independently represents a hydrogen atom, an aryl group, or an alkyl group; or $R_1$ and $R_2$ together represent the atoms completing a cycloalkyl group; and $R_3$ and $R_4$ each independently represents an aryl group, which is in turn substituted with a diaryl substituted amino group, as indicated by structural formula (C):

(C)

wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines is the tetraaryldiamines. Desirable tetraaryldiamines include two diarylamino groups, such as indicated by formula (C), linked through an arylene group. Useful tetraaryldiamines include those represented by formula (D):

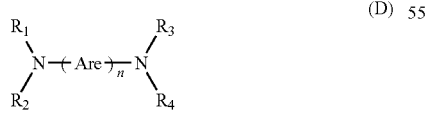
(D)

wherein each Are is an independently selected arylene group, such as a phenylene or anthracene moiety, n is selected from 1 to 4, and $R_1$-$R_4$ are independently selected aryl groups.

In a typical embodiment, at least one of $R_1$-$R_4$ is a polycyclic fused ring structure, e.g., a naphthalene.

The various alkyl, alkylene, aryl, and arylene moieties of the foregoing structural formulas (A), (B), (C), and (D) can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms, such as cyclopentyl, cyclohexyl, and cycloheptyl ring structures. The aryl and arylene moieties are usually phenyl and phenylene moieties.

Representative examples of the useful compounds include the following:

4,4'-Bis[N-(1-naphthyl)-N-phenylamino]biphenyl (NPB);
4,4'-Bis[N-(1-naphthyl)-N-(2-naphthyl)amino]biphenyl (TNB);
4,4'-Bis[N-(3-methylphenyl)-N-phenylamino]biphenyl (TPD);
4,4'-Bis-diphenylamino-terphenyl;
2,6,2',6'-tetramethyl-N,N,N',N'-tetraphenyl-benzidine.

In one suitable embodiment the hole transporting co-host comprises a material of formula (E):

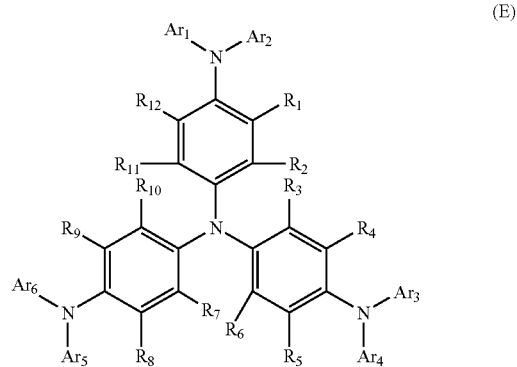
(E)

In formula (E), $Ar_1$-$Ar_6$ independently represent aromatic groups, for example, phenyl groups or tolyl groups;

$R_1$-$R_{12}$ independently represent hydrogen or independently selected substituent, for example an alkyl group containing from 1 to 4 carbon atoms, an aryl group, a substituted aryl group.

Examples of the suitable materials include, but are not limited to:

4,4',4''-tris[(3-methylphenyl)phenylamino]triphenylamine (MTDATA);
4,4',4''-tris(N,N-diphenyl-amino)triphenylamine (TDATA);
N,N-bis[2,5-dimethyl-4-[(3-methylphenyl)phenylamino] phenyl]-2,5-dimethyl-N'-(3-methylphenyl)-N'-phenyl-1, 4-benzenediamine.

In one desirable embodiment the hole transporting co-host comprises a material of formula (F):

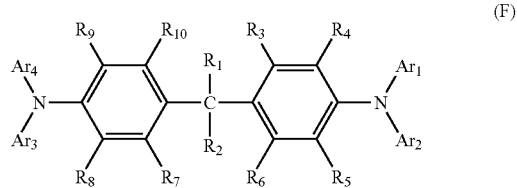
(F)

In formula (F), $R_1$ and $R_2$ represent substituents, provided that $R_1$ and $R_2$ can join to form a ring. For example, $R_1$ and $R_2$ can be methyl groups or join to form a cyclohexyl ring;

$Ar_1$-$Ar_4$ represent independently selected aromatic groups, for example phenyl groups or tolyl groups;

$R_3$-$R_{10}$ independently represent hydrogen, alkyl, substituted alkyl, aryl, substituted aryl group.

Examples of suitable materials include, but are not limited to:

1,1-Bis(4-(N,N-di-p-tolylamino)phenyl)cyclohexane (TAPC);
1,1-Bis(4-(N,N-di-p-tolylamino)phenyl)cyclopentane;
4,4'-(9H-fluoren-9-ylidene)bis[N,N-bis(4-methylphenyl)-benzenamine;
1,1-Bis(4-(N,N-di-p-tolylamino)phenyl)-4-phenylcyclohexane;
1,1-Bis(4-(N,N-di-p-tolylamino)phenyl)-4-methylcyclohexane;
1,1-Bis(4-(N,N-di-p-tolylamino)phenyl)-3-phenylpropane;
Bis[4-(N,N-diethylamino)-2-methylphenyl](4-methylpenyl)methane;
Bis[4-(N,N-diethylamino)-2-methylphenyl](4-methylphenyl)ethane;
4-(4-Diethyl aminophenyl)triphenylmethane;
4,4'-Bis(4-diethylaminophenyl)diphenylmethane.

A useful class of triarylamines suitable for use as the hole transporting co-host includes carbazole derivatives such as those represented by formula (G):

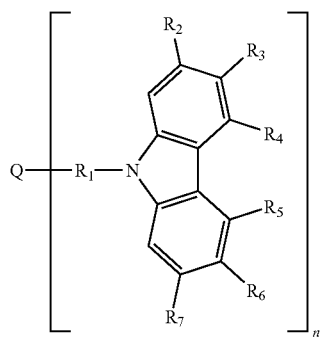

In formula (G), Q independently represents nitrogen, carbon, an aryl group, or substituted aryl group, preferably a phenyl group;

$R_1$ is preferably an aryl or substituted aryl group, and more preferably a phenyl group, substituted phenyl, biphenyl, substituted biphenyl group;

$R_2$ through $R_7$ are independently hydrogen, alkyl, phenyl or substituted phenyl group, aryl amine, carbazole, or substituted carbazole;

and n is selected from 1 to 4.

Another useful class of carbazoles satisfying structural formula (G) is represented by formula (H):

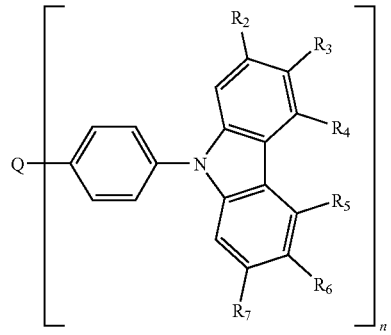

wherein n is an integer from 1 to 4;

Q is nitrogen, carbon, an aryl, or substituted aryl;

$R_2$ through $R_7$ are independently hydrogen, an alkyl group, phenyl or substituted phenyl, an aryl amine, a carbazole and substituted carbazole.

Illustrative of useful substituted carbazoles are the following:

4-(9H-carbazol-9-yl)-N,N-bis[4-(9H-carbazol-9-yl)phenyl]-benzenamine (TCTA);
4-(3-phenyl-9H-carbazol-9-yl)-N,N-bis[4(3-phenyl-9H-carbazol-9-yl)phenyl]-benzenamine;
9,9'-[5'-[4-(9H-carbazol-9-yl)phenyl][1,1':3',1"-terphenyl]-4,4"-diyl]bis-9H-carbazole.

In one suitable embodiment the hole transporting co-host comprises a material of formula (I):

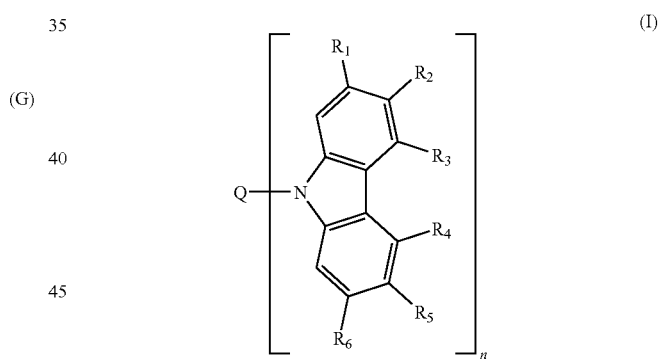

In formula I, n is selected from 1 to 4;

Q independently represents phenyl group, substituted phenyl group, biphenyl, substituted biphenyl group, aryl, or substituted aryl group;

$R_1$ through $R_6$ are independently hydrogen, alkyl, phenyl or substituted phenyl, aryl amine, carbazole, or substituted carbazole.

Examples of suitable materials are the following:

9,9'-(2,2'-dimethyl[1,1'-biphenyl]-4,4'-diyl)bis-9H-carbazole (CDBP);
9,9'-[1,1'-biphenyl]-4,4'-diylbis-9H-carbazole (CBP);
9,9'-(1,3-phenylene)bis-9H-carbazole (mCP);
9,9'-(1,4-phenylene)bis-9H-carbazole;
9,9',9"-(1,3,5-benzenetriyl)tris-9H-carbazole;
9,9'-(1,4-phenylene)bis[N,N,N',N'-tetraphenyl-9H-carbazole-3,6-diamine;
9-[4-(9H-carbazol-9-yl)phenyl]-N,N-diphenyl-9H-carbazol-3-amine;

9,9'-(1,4-phenylene)bis[N,N-diphenyl-9H-carbazol-3-amine;

9-[4-(9H-carbazol-9-yl)phenyl]-N,N,N',N'-tetraphenyl-9H-carbazole-3,6-diamine.

The optimum concentration of the hole transporting co-host in a preferred embodiment of the present invention may be determined by experimentation and may be within the range 10 to 60 weight % of the total of the hole- and electron transporting co-host materials in the light emitting layer, and is often found to be in the range 15 to 30 wt. %.

The desirable electron transporting co-host may be any suitable electron transporting compound, such as benzazole, phenanthroline, 1,3,4-oxadiazole, triazole, triazine, or triarylborane, as long as it has a triplet energy that is higher than that of the phosphorescent emitter to be employed.

A preferred class of benzazoles is described by Jianmin Shi et al. in U.S. Pat. Nos. 5,645,948 and 5,766,779. Such compounds are represented by structural formula (J):

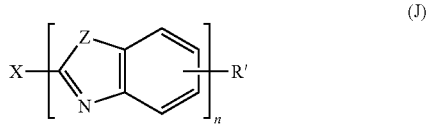

In formula (J), n is selected from 2 to 8;

Z is independently O, NR or S;

R and R' are individually hydrogen; alkyl of from 1 to 24 carbon atoms, for example, propyl, t-butyl, heptyl, and the like; aryl or hetero-atom substituted aryl of from 5 to 20 carbon atoms, for example, phenyl and naphthyl, furyl, thienyl, pyridyl, quinolinyl and other heterocyclic systems; or halo such as chloro, fluoro; or atoms necessary to complete a fused aromatic ring; and X is a linkage unit consisting of carbon, alkyl, aryl, substituted alkyl, or substituted aryl, which conjugately or unconjugately connects the multiple benzazoles together.

An example of a useful benzazole is 2,2',2''-(1,3,5-phenylene)tris[1-phenyl-1H-benzimidazole] (TPBI) represented by a formula (K) shown below:

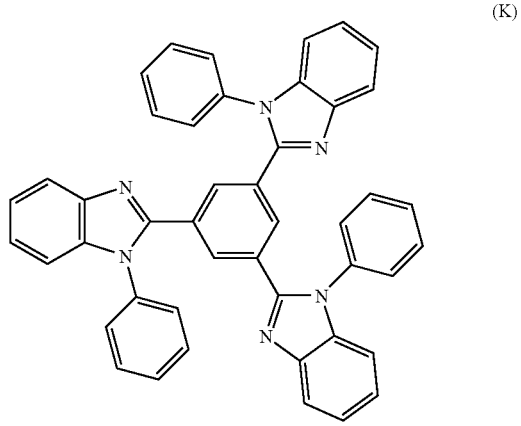

Another class of the electron transporting materials suitable for use as a co-host includes various substituted phenanthrolines as represented by formula (L):

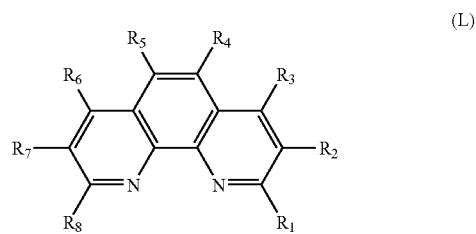

In formula (L), $R_1$-$R_8$ are independently hydrogen, alkyl group, aryl or substituted aryl group, and at least one of $R_1$-$R_8$ is aryl group or substituted aryl group.

Examples of suitable materials are 2,9-dimethyl-4,7-diphenyl-phenanthroline (BCP) (see formula (M)) and 4,7-diphenyl-1,10-phenanthroline (Bphen) (see formula (N)).

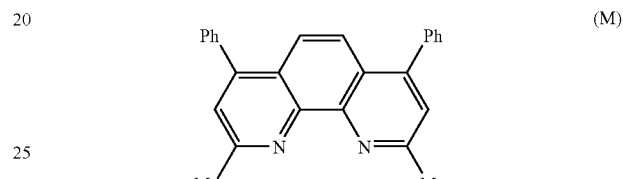

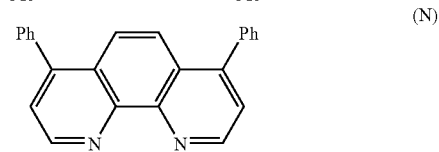

The triarylboranes that function as the electron transporting co-host in the present invention may be selected from compounds having the chemical formula (O):

wherein $Ar_1$ to $Ar_3$ are independently an aromatic hydrocarbocyclic group or an aromatic heterocyclic group which may have a substituent. It is preferable that compounds having the above structure are selected from formula (P):

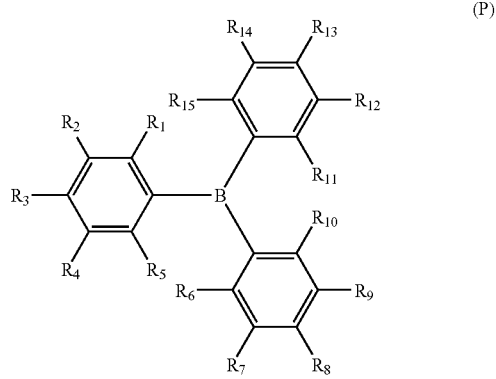

wherein $R_1$-$R_{15}$ are independently hydrogen, fluoro, cyano, trifluoromethyl, sulfonyl, alkyl, aryl or substituted aryl group.

Specific representative embodiments of the triarylboranes include:

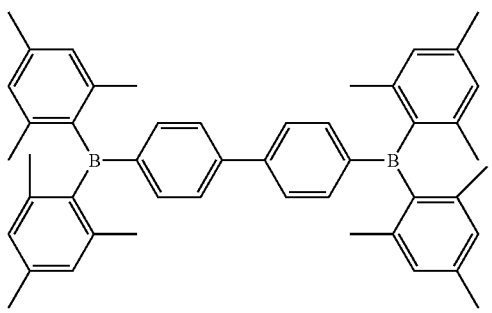

(Q)

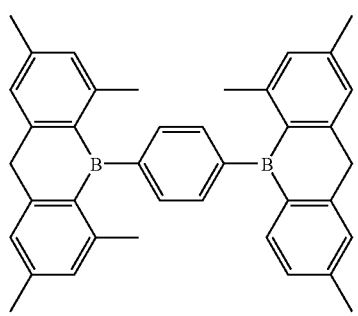

(R)

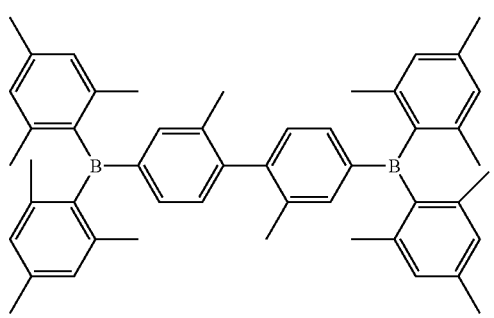

(S)

The electron transporting co-host in the present invention may be selected from substituted 1,3,4-oxadiazoles. Illustrative of the useful substituted oxadiazoles are the following:

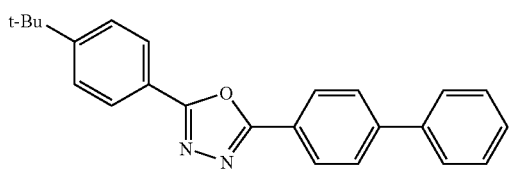

(T)

-continued

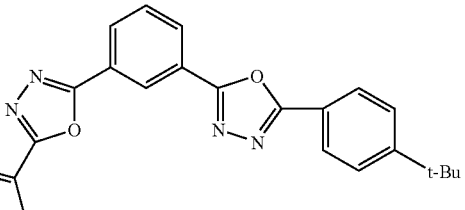

(U)

The electron transporting co-host in the present invention also may be selected from substituted 1,2,4-triazoles. An example of a useful triazole is 3-phenyl-4-(1-naphtyl)-5-phenyl-1,2,4-triazole represented by formula (V):

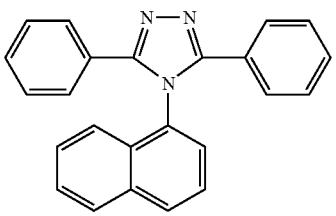

(V)

The electron transporting co-host in the present invention also may be selected from substituted 1,3,5-triazines. Examples of suitable materials are:

2,4,6-tris(diphenylamino)-1,3,5-triazine;
2,4,6-tricarbazolo-1,3,5-triazine;
2,4,6-tris(N-phenyl-2-naphthylamino)-1,3,5-triazine;
2,4,6-tris(N-phenyl-1-naphthylamino)-1,3,5-triazine;
4,4',6,6'-tetraphenyl-2,2'-bi-1,3,5-triazine;
2,4,6-tris([1,1':3',1''-terphenyl]-5'-yl)-1,3,5-triazine.

The optimum concentration of the electron transporting co-host in a preferred embodiment of the present invention may be determined by experimentation and may be within the range from 40 to 90 weight %, and is often found to be in the range from 70 to 85 weight %.

Phosphorescent Materials

Phosphorescent materials of Formulas I-X may be used singly or in combination with other phosphorescent materials, either in the same or different layers. The light-emitting phosphorescent guest material(s) is typically present in an amount of from 1 to 20 by weight % of the light-emitting layer, and conveniently from 2 to 8% by weight of the light-emitting layer. In some embodiments, the phosphorescent complex guest material(s) may be attached to one or more host materials. The host materials may further be polymers. For convenience, the phosphorescent complex guest material may be referred to herein as a phosphorescent material.

Particularly useful phosphorescent materials are described by Formula 1 below.

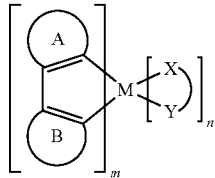

(1)

wherein:
A is a substituted or unsubstituted heterocycle ring cont at least one N atom;
B is a substituted or unsubstituted aromatic or heteroaromatic ring, or ring containing a vinyl carbon bonded to M;
X—Y is an anionic bidentate ligand;
m is an integer from 1 to 3 and n in an integer from 0 to 2 such that 3 + n = 3 for M = Rh or Ir; or , is an integer from 1 to 2 and n in an integer from 0 to1 such that m + n = 2 for M = Pt, Pd.

Compounds according to Formula 1 may be referred to as C,N-cyclometallated complexes to indicate that the central metal atom is contained in a cyclic unit formed by bonding the metal atom to carbon and nitrogen atoms of one or more ligands. Examples of heterocyclic ring A in Formula 1 include substituted or unsubstituted pyridine, quinoline, isoquinoline, pyrimidine, indole, indazole, thiazole, and oxazole rings. Examples of ring B in Formula 1 include substituted or unsubstituted phenyl, napthyl, thienyl, benzothienyl, furanyl rings. Ring B in Formula 1 may also be a N-containing ring such as pyridine, with the proviso that the N-containing ring bonds to M through a C atom as shown in Formula 1 and not the N atom.

An example of a tris-C,N-cyclometallated complex according to Formula 1 with m=3 and n=0 is tris(2-phenyl-pyridinato-N,C$^{2'}$-)Iridium(III), shown below in stereodiagrams as facial (fac-) or meridional (mer-) isomers.

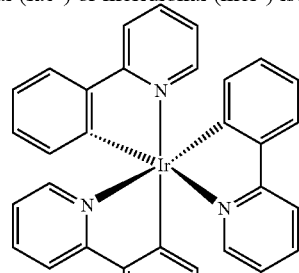

Fac

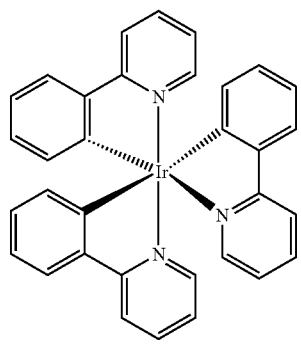

Mer

Generally, facial isomers are preferred since they are often found to have higher phosphorescent quantum yields than the meridional isomers. Additional examples of tris-C,N-cyclometallated phosphorescent materials according to Formula 1 are tris(2-(4'-methylphenyl)pyridinato-N,C$^{2'}$)Iridium(III), tris(3-phenylisoquinolinato-N,C$^{2'}$)Iridium(III), tris(2-phenylquinolinato-N,C$^{2'}$)Iridium(III), tris(1-phenylisoquinolinato-N,C$^{2'}$)Iridium(III), tris(1-(4'-methylphenyl)isoquinolinato-N,C$^{2'}$)Iridium(III), tris(2-(4,6-diflourophenyl)-pyridinato-N,C$^{2'}$)Iridium(III), tris(2-(5'-phenyl)-phenyl) pyridinato-N,C$^{2'}$)Iridium(III), tris(2-(2'-benzothienyl) pyridinato-N,C$^{3'}$)Iridium(III), tris(2-phenyl-3,3'dimethyl) indolato-N,C$^{2'}$)Ir(III), tris(1-phenyl-1H-indazolato-N,C$^{2'}$)Ir (III).

Tris-C,N-cyclometallated phosphorescent materials also include compounds according to Formula 1 wherein the monoanionic bidentate ligand X—Y is another C,N-cyclometallating ligand. Examples include bis(1-phenylisoquinolinato-N,C$^{2'}$)(2-phenylpyridinato-N,C$^{2'}$)Iridium(III) and bis (2-phenylpyridinato-N,C$^{2'}$) (1-phenylisoquinolinato-N,C$^{2'}$) Iridium(III).

Suitable phosphorescent materials according to Formula 1 may in addition to the C,N-cyclometallating ligand(s) also contain monoanionic bidentate ligand(s) X—Y that are not C,N-cyclometallating. Common examples are beta-diketonates such as acetylacetonate, and Schiff bases such as picolinate. Examples of such mixed ligand complexes according to Formula 1 include bis(2-phenylpyridinato-N,C$^{2'}$)Iridium(III) (acetylacetonate), bis(2-(2'-benzothienyl)pyridinato-N,C$^{3'}$) Iridium(III)(acetylacetonate), and bis(2-(4,6-diflourophenyl)-pyridinato-N,C$^{2'}$)Iridium(III)(picolinate).

Other important phosphorescent materials according to Formula 1 include C,N-cyclometallated Pt(II) complexes such as cis-bis(2-phenylpyridinato-N,C$^{2'}$)platinum(II), cis-bis(2-(2'-thienyl)pyridinato-N,C$^{3'}$) platinum(II), cis-bis(2-(2'-thienyl)quinolinato-N,C$^{5'}$) platinum(II), or (2-(4,6-difluorophenyl)pyridinato-N,C$^{2'}$) platinum (II) (acetylacetonate).

The emission wavelengths (color) of C,N-cyclometallated phosphorescent materials according to Formula 1 are governed principally by the lowest energy optical transition of the complex and hence by the choice of the C,N-cyclometallating ligand. For example, 2-phenyl-pyridinato-N,C$^{2'}$ complexes are typically green emissive while 1-phenyl-isoquinolino-lato-N,C$^{2'}$ complexes are typically red emissive. In the case of complexes having more than one C,N-cyclometallating ligand, the emission will be that of the ligand having the property of longest wavelength emission. Emission wavelengths may be further shifted by the effects of substituent groups on the C,N-cyclometallating ligands. For example, substitution of electron donating groups at appropriate positions on the N-containing ring A or electron withdrawing groups on the C-containing ring B tend to blue-shift the emission relative to the unsubstituted C,N-cyclometallated ligand complex. Selecting a monodentate anionic ligand X,Y in Formula 1 having more electron withdrawing properties also tends to blue-shift the emission of a C,N-cyclometallated ligand complex. Examples of complexes having both monoanionic bidentate ligands possessing electron-withdrawing properties and electron-withdrawing substituent groups on the C-containing ring B include bis(2-(4,6-difluorophenyl)-pyridinato-N,C$^{2'}$)iridium(III)(picolinate) and bis (2-(4,6-difluorophenyl)-pyridinato-N,C$^{2'}$)iridium(III)(tetrakis-pyrazolato borate).

The central metal atom in phosphorescent materials according to Formula 1 may be Rh or Ir for (m+n=3) and Pd or Pt (m+n=2). Preferred metal atoms are Ir and Pt since these tend to give higher phosphorescent quantum efficiencies according to the stronger spin-orbit coupling interactions generally obtained with elements in the third transition series.

Other phosphorescent materials that do not involve C,N-cyclometallating ligands are known. Phosphorescent complexes of Pt(II), Ir(I), and Rh(I) with maleonitriledithiolate have been reported (C. E. Johnson et al, J. Am. Chem. Soc., 105, 1795-1802 (1983)). Re(I) tricarbonyl diimine complexes are also known to be highly phosphorescent (M. Wrighton and D. L. Morse, J. Am. Chem. Soc., 96, 998-1003 (1974); D. J. Stufkens, Comments Inorg. Chem., 13,359-385 (1992); V. W. W. Yam, Chem. Commun., 2001, 789-796)). Os(II) complexes containing a combination of ligands including cyano ligands and bipyridyl or phenanthroline ligands have also been demonstrated in a polymer OLED (Y. Ma et al, Synthetic Metals, 94, 245-248 (1998)).

Porphyrin complexes such as 2,3,7,8,12,13,17,18-octa-ethyl-21H, 23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al., Chem Lett., 657 (1990); J Alloys and Compounds, 192, 30-33 (1993); Jpn J Appl Phys, 35, L394-6 (1996) and Appl. Phys. Lett., 65, 2124 (1994)). Additional information on suitable phosphorescent materials, incorporated herein by reference, can be found in U.S. Pat. No. 6,303,238 B1, WO 00/57676, WO 00/70655, WO 01/41512 A1, US 2002/0182441 A1, US 2003/0017361 A1, US 2003/0072964 A1, U.S. Pat. Nos. 6,413,656 B1, 6,687, 266 B1, US 2004/0086743 A1, US 2004/0121184 A1, US 2003/0059646 A1, US 2003/0054198 A1, EP 1 239 526 A2, EP 1 238 981 A2, EP 1 244 155 A2, US 2002/0100906 A1, US 2003/0068526 A1, US 2003/0068535 A1, JP 2003073387A, JP 2003 073388A, U.S. Pat. No. 6,677,060 B2, US 2003/0235712 A1, US 2004/0013905 A1, U.S. Pat. Nos. 6,733,905 B2, 6,780,528 B2, US 2003/0040627 A1, JP 2003059667A, JP 2003073665A, US 2002/0121638 A1, EP 1371708A1, US 2003/010877 A1, WO 03/040256 A2, US 2003/0096138 A1, US 2003/0173896 A1, U.S. Pat. No. 6,670,645 B2, US 2004/0068132 A1, WO 2004/015025 A1, US 2004/0072018 A1, US 2002/0134984 A1, WO 03/079737 A2, WO 2004/020448 A1, WO 03/091355 A2, U.S. Ser. Nos. 10/729,402, 10/729, 712, 10/729,738, 10/729,238, 10/729,246 (now allowed), U.S. Ser. No. 10/729,207 (now allowed), and U.S. Ser. No. 10/729,263 (now allowed).

Blocking Layers

In addition to suitable hosts, an OLED device employing a phosphorescent material often requires at least one exciton blocking layer 108 and/or a hole blocking layer 110 to help confine the excitons or electron-hole recombination centers to the light-emitting layer comprising the host and phosphorescent material. In one embodiment, such a blocking layer would be placed between the electron-transporting layer and the light-emitting layer—see FIG. 1, layer 110. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO 00/70655 and WO 01/93642. Two examples of useful materials are bathocuproine (BCP) and bis(2-methyl-8-quinolinolato)(4-phenylphenolato)Aluminum(III) (BAlQ).

A preferred embodiment of an OLED device employing a phosphorescent emitter according to the present invention may include at least one exciton blocking layer, 108 (FIG. 1), placed adjacent the light emitting layer 109 on the anode side, to help confine triplet excitons to the light emitting layer comprising a host or co-hosts and a phosphorescent emitter. In order that the exciton blocking layer be capable of confining triplet excitons, the material or materials of this layer should have triplet energies that exceed that of the phosphorescent emitter. Otherwise, if the triplet energy level of any material in the layer adjacent the light emitting layer is lower than that of the phosphorescent emitter, often that material will quench excited states in the light emitting layer, decreasing device luminous efficiency. In some cases it is also desirable that the exciton blocking layer also help to confine electron-hole recombination events to the light emitting layer by blocking the escape of electrons from the light emitting layer into the exciton blocking layer. In order that the exciton blocking layer have this electron blocking property, the material or materials of this layer should have solid-state electron affinities that exceed the electron affinities of the materials in the light emitting layer by at least 0.1 eV and preferably by at least 0.2 eV.

Triplet energy is conveniently measured by any of several means, as discussed for instance in S. L. Murov, I. Carmichael, and G. L. Hug, Handbook of Photochemistry, 2nd ed. (Marcel Dekker, New York, 1993).

The triplet state of a compound can also be calculated. The triplet state energy for a molecule is obtained as the difference between the ground state energy (E(gs)) of the molecule and the energy of the lowest triplet state (E(ts)) of the molecule, both given in eV. These energies are obtained using the B3LYP method as implemented in the Gaussian 98 (Gaussian, Inc., Pittsburgh, Pa.) computer program. The basis set for use with the B3LYP method is defined as follows: MIDI! for all atoms for which MIDI! is defined, 6-31G* for all atoms defined in 6-31G* but not in MIDI!, and either the LACV3P or the LANL2DZ basis set and pseudopotential for atoms not defined in MIDI! or 6-31G*, with LACV3P being the preferred method. For any remaining atoms, any published basis set and pseudopotential may be used. MIDI!, 6-31 G* and LANL2DZ are used as implemented in the Gaussian98 computer code and LACV3P is used as implemented in the Jaguar 4.1 (Schrodinger, Inc., Portland Oreg.) computer code. The energy of each state is computed at the minimum-energy geometry for that state. The difference in energy between the two states is further modified by equation (1) to give the triplet state energy (E(t)):

$$E(t)=0.84*(E(ts)-E(gs))+0.35 \qquad \text{(eq. 1)}.$$

For polymeric or oligomeric materials, it is sufficient to compute the triplet energy over a monomer or oligomer of sufficient size so that additional units do not substantially change the computed triplet energy.

The calculated values for the triplet state energy of a given compound may typically show some deviation from the experimental values. Thus, the calculations should be used only as a rough guide in the selection of appropriate materials.

The exciton blocking layer can be between 1 and 500 nm thick and suitably between 10 and 300 nm thick. Thicknesses in this range are relatively easy to control in manufacturing.

In addition to having high triplet energy, the exciton blocking layer 108 must be capable of transporting holes to the light emitting layer 109. A hole transporting material deposited in said exciton blocking layer between the anode and the light emitting layer may be the same or different from a hole transporting compound described previously to be used as a co-host according to a preferred embodiment of the invention provided that the triplet energy of the exciton blocking material is greater than that of the phosphorescent emitter. The hole transporting material deposited in said exciton blocking layer may be selected from the same set of hole transporting materials previously described for use as hole-transporting co-hosts. Additional materials that may be used as exciton blocking layer 108 that are metal complexes such as fac-tris (1-phenylpyrazolato-N,C2)iridium(III) (Irppz) are disclosed in US 20030175553. The exciton blocking layer may include more than one compound, deposited as a blend or divided into separate layers.

Electron-Transporting Layer (ETL)

Preferred thin film-forming materials for use in forming the electron-transporting layer of the organic EL elements of this invention are metal chelated oxinoid compounds, including chelates of oxine itself (also commonly referred to as 8-quinolinol or 8-hydroxyquinoline). Such compounds help to inject and transport electrons, exhibit high levels of performance, and are readily fabricated in the form of thin films. Exemplary oxinoid compounds were listed previously.

Other electron-transporting materials include various butadiene derivatives as disclosed in U.S. Pat. No. 4,356,429 and various heterocyclic optical brighteners as described in U.S. Pat. No. 4,539,507. Benzazoles and triazines are also useful electron-transporting materials.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, L1-doped Alq, as disclosed in U.S. Pat. No. 6,013,384, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776, 622, 5,776,623, 5,714,838, 5,969,474, 5,739,545, 5,981,306, 6,137,223, 6,140,763, 6,172,459, EP 1 076 368, U.S. Pat. Nos. 6,278,236, and 6,284,393. Cathode materials are typically deposited by any suitable methods such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Other Common Organic Layers and Device Architecture

In some instances, layers 109 and 111 can optionally be collapsed into a single layer that serves the function of supporting both light emission and electron transportation. It also known in the art that emitting dopants may be added to the hole-transporting layer, which may serve as a host. Multiple dopants may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, EP 1 182 244, U.S. Pat. Nos. 5,683,823, 5,503,910, 5,405, 709, and 5,283,182, US 20020186214, US 20020025419, US 20040009367, and U.S. Pat. No. 6,627,333.

Additional layers such as exciton, electron and hole-blocking layers as taught in the art may be employed in devices of this invention. Hole-blocking layers are commonly used to improve efficiency of phosphorescent emitter devices, for example, as in US 20020015859, WO 00/70655A2, WO 01/93642A1, US 20030068528 and US 20030175553 A1.

This invention may be used in so-called stacked device architecture, for example, as taught in U.S. Pat. Nos. 5,703, 436 and 6,337,492.

Deposition of Organic Layers

The organic materials mentioned above are suitably deposited through a vapor-phase method such as sublimation, but can be deposited from a fluid, for example, from a solvent with an optional binder to improve film formation. If the material is a polymer, solvent deposition is useful but other methods can be used, such as sputtering or thermal transfer from a donor sheet. The material to be deposited by sublimation can be vaporized from a sublimation "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimation boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon. In sealing an OLED device in an inert environment, a protective cover can be attached using an organic adhesive, a metal solder, or a low melting temperature glass. Commonly, a getter or desiccant is also provided within the sealed space. Useful getters and desiccants include, alkali and alkaline metals, alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti glare or anti-reflection coatings over the display, providing a polarizing medium over the display, or providing colored, neutral density, or color conversion filters in functional relationship with the light emitting areas of the display. Filters, polarizers, and anti-glare or anti-reflection coatings can also be provided over a cover or as part of a cover.

The OLED device may have a microcavity structure. In one useful example, one of the metallic electrodes is essentially opaque and reflective; the other one is reflective and semi-transparent. The reflective electrode is preferably selected from Au, Ag, Mg, Ca, or alloys thereof. Because of the presence of the two reflecting metal electrodes, the device has a microcavity structure. The strong optical interference in this structure results in a resonance condition. Emission near the resonance wavelength is enhanced and emission away from the resonance wavelength is depressed. The optical path length can be tuned by selecting the thickness of the organic layers or by placing a transparent optical spacer between the electrodes. For example, an OLED device of this invention can have ITO spacer layer placed between a reflective anode and the organic EL media, with a semitransparent cathode over the organic EL media.

EXAMPLES

Synthetic Example 1

Preparation of metal complex Inv-1

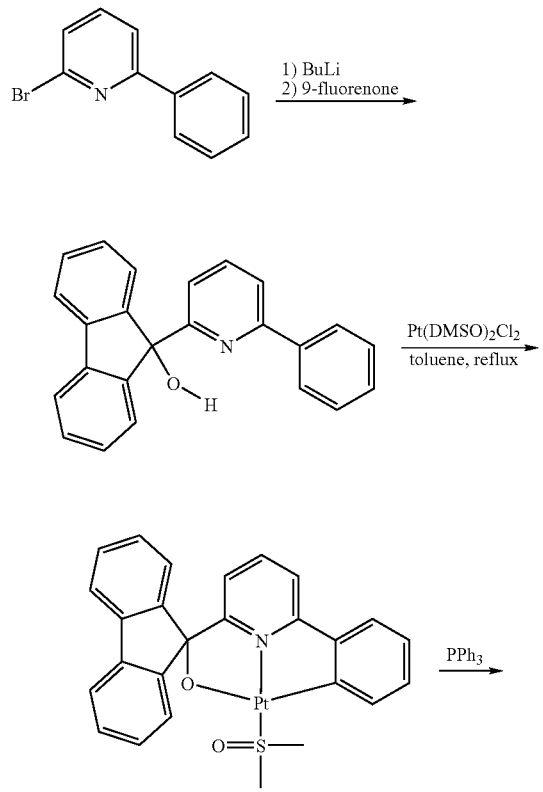

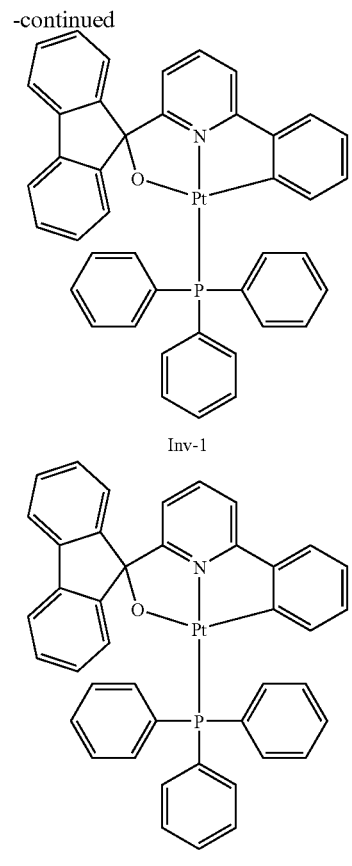

Preparation of 2-brom-6-phenylpyridine: To a solution of 2,6-dibromopyridine (8.53 g, 36 mmol) and Pd(PPh$_3$)$_4$ (1.61 g, 1.4 mmol) in anhydrous THF (100 mL) was added a solution of PhMgBr (30 mL, 1.0 M in THF, 30 mmol) at 0° C. (ice-water bath) under nitrogen atmosphere over 1.5 h. After the addition, the reaction mixture was stirred at 0° C. for 2 h then warmed to room temperature. The mixture was poured into water (200 mL) and extracted with ethyl acetate (2×200 mL). The combined organic extracts were washed with water and brine, dried over MgSO$_4$, filtered, and evaporated. The residue was purified by column to give a mixture of 2,6-dibromopyridine, 2-bromo-6-phenylpyridine, and 2,6-diphenylpyridine. Recrystallizations of the crude products yielded 2-bromo-6-phenylpyridine, 2.77 g, 40%. 2-Bromo-6-phenylpyridine can also be prepared according to the literature procedure from 2-phenylpyridine (Philippe Gros and Yves Fort, J. Org. Chem. 2003, 68, 2028-2029).

Preparation of 9-(6-phenylpyridin-2-yl)-9H-fluoren-9-ol: A solution of 2-bromo-6-phenylpyridine (1.79 g, 7.65 mmol) in anhydrous THF (50 mL) was cooled to −78° C. with a dry ice-acetone bath. To this solution was added dropwise a solution of n-butyllithium (5.26 mL, 1.6 M, 8.4 mmol). After the addition, the resultant brown solution was stirred at −78° C. for 20 min. A solution of 9-fluorenone (1.66 g, 9.24 mmol) in anhydrous THF (10 mL) was added slowly via a syringe. The mixture was stirred at −78° C. for 30 min then at room temperature for 2 h. The reaction mixture was quenched with water (200 mL), extracted with ethyl acetate (3×100 mL). Some precipitates were collected by filtration, which turned out to be the desired product, 0.83 g. The organic extracts were combined and washed with brine, dried over MgSO$_4$, filtered. The filtrate was evaporated and the residue was thoroughly washed with ether and heptane and dried in air, 1.05 g. The total yield was 73% (1.88 g). MS: [M+1] 336.

Preparation of metal complex Inv-1: To a suspension of Pt(DMSO)$_2$Cl$_2$ (443 mg, 1.05 mmol) in 100 ml of anhydrous toluene was added 9-(6-phenylpyridin-2-yl)-9H-fluoren-9-ol (387 mg, 1.15 mmol) and a solution of NaOAc in methanol (2 M, 4 mL). The mixture was refluxed for 5 h. The solvents were removed under reduced pressure and the residue was treated with methylene chloride (100 mL) and filtered through a celite-covered frit. The filtrate was stirred with triphenylphosphine (390 mg, 1.5 mmol) at room temperature for 1 h. The crude product was purified by chromatography on silica gel column with methylene chloride-ethyl acetate (9:1) as an eluent and by recrystallization from methylene chloride-heptane to give yellow green crystals, Inv-1, 0.28 g, 35%. The structure of the complex has been confirmed by X-ray single crystal structure analysis. MS: M 790, 791, 792.

Synthetic Example 2

Synthesis of Metal Complex Comp-1

A comparative metal complex Comp-1 was prepared according to the literature procedure as shown bellow (Gareth W. V. Vave, Nathaniel W. Alcock, and Jonathan P. Rourke, *Organometallics* 1999, 18, 1801-1803; Wei Lu, Michael C. W. Chan, Kung-Kai Cheung, and Chi-Ming Che, *Organometallics* 2001, 20, 2477-2486).

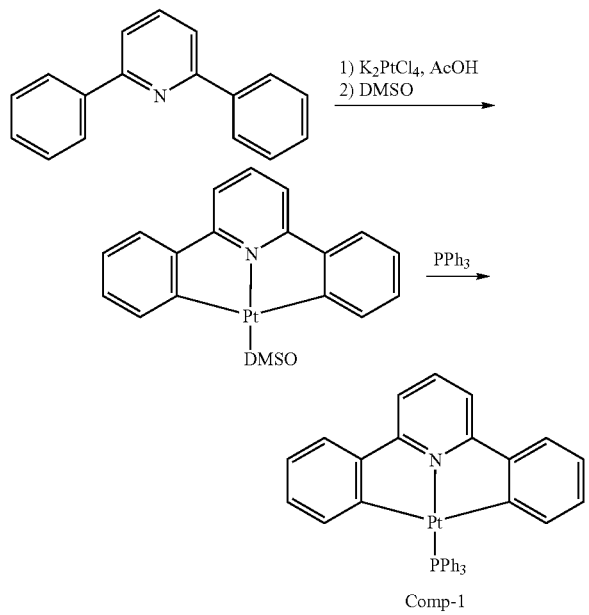

Comp-1

Figure 2:
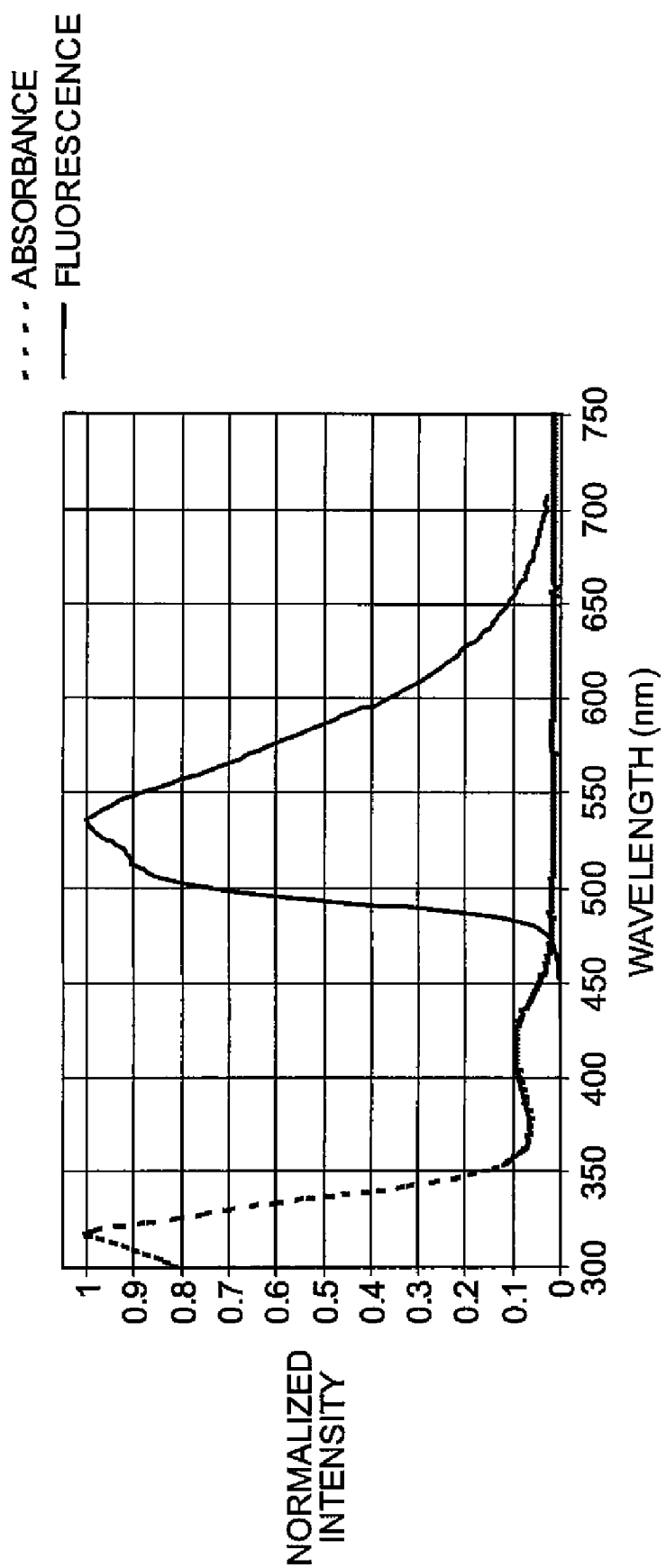
FIG. 2 shows the normalized absorption (dashed line) and emission (solid line) intensity as a function of wavelength for organometallic complex Inv-1 in solution of methylene chloride.

The photoluminescence quantum yields of the invention complex Inv-1 and the comparative Comp-1 are shown in Table 1. It can be seen from the table that the quantum yield of Inv-1 is much higher than that of Comp-1. Comp-1 is essentially non-emissive in solution of methylene chloride at room temperature therefore is not a suitable candidate for a phosphorescent emitter in OLED device. The phosphorescence characteristic of Inv-1 was also indicated by the difference of the quantum yields of the sample prior to and after nitrogen purge, 2% vs 71% as shown in Table 1. Absorption and emission spectra of Inv-1 in methylene chloride are shown in FIG. 2.

TABLE 1

The photoluminescence quantum yields in solution

| Sample | Temperature | Q.Y. (%) After N$_2$ purged | Q.Y. (%) Before N$_2$ purge | Type |
|---|---|---|---|---|
| Inv-1 | Room temperature | 71 | 2 | Invention |
| Comp-1 | Room temperature | <1 | — | Comparison |

Device Examples 3-7

An EL device (Example 3) satisfying the requirements of the invention was constructed in the following manner:

1. A glass substrate coated with an 85 nm layer of indium-tin oxide (ITO) as the anode was sequentially ultrasonicated in a commercial detergent, rinsed in deionized water, degreased in toluene vapor and exposed to oxygen plasma for about 1 min.
2. Over the ITO was deposited a 1 nm fluorocarbon (CFx) hole-injecting layer (HIL) by plasma-assisted deposition of CHF$_3$.
3. A hole-transporting layer (HTL) of N,N'-di-1-naphthyl-N,N'-diphenyl-4,4'-diaminobiphenyl (NPB) having a thickness of 75 nm was then evaporated from a tantalum boat.
4. A 35 nm light-emitting layer (LEL) of 4,4'-N,N'-dicarbazole-biphenyl (CBP) and organometallic complex (Inv-1) (2% doped) were then deposited onto the hole-transporting layer. These materials were also evaporated from tantalum boats.
5. A hole-blocking layer of bis(2-methyl-quinolinolate)(4-phenylphenolate)aluminum (Balq) having a thickness of 10 nm was then evaporated from a tantalum boat.
6. A 40 nm electron-transporting layer (ETL) of tris(8-quinolinolato)aluminum (III) (AlQ$_3$) was then deposited onto the light-emitting layer. This material was also evaporated from a tantalum boat.
7. On top of the AlQ$_3$ layer was deposited a 220 nm cathode formed of a 10:1 volume ratio of Mg and Ag.

The above sequence completed the deposition of the EL device. The device was then hermetically packaged in a dry glove box for protection against ambient environment.

Examples 4, 5, 6, and 7 were fabricated in an identical manner to Example 3 except emitter Inv-1 was used at levels indicated in Table 2. Example 8 was fabricated in an identical manner to Example 1 except compound Inv-1 was not included. The cells thus formed were tested for luminance and color at an operating current of 20 mA/cm$^2$ and the results are reported in Table 2 in the form of luminance, efficiency, life time, and CIE (Commission Internationale de L'Eclairage) coordinates.

TABLE 2

Evaluation Results for EL devices.

| Example | Inv-1 (%) | Luminance (cd/m$^2$) | Efficiency W/A | CIEx | CIEy | Type |
|---|---|---|---|---|---|---|
| 3 | 2 | 453 | 0.018 | 0.261 | 0.489 | Invention |
| 4 | 4 | 611 | 0.023 | 0.275 | 0.528 | Invention |
| 5 | 6 | 773 | 0.027 | 0.288 | 0.561 | Invention |
| 6 | 8 | 828 | 0.028 | 0.305 | 0.586 | Invention |

TABLE 2-continued

Evaluation Results for EL devices.

| Example | Inv-1 (%) | Luminance (cd/m²) | Efficiency W/A | CIEx | CIEy | Type |
|---|---|---|---|---|---|---|
| 7 | 10 | 805 | 0.028 | 0.294 | 0.577 | Invention |
| 8 | 0 | 119 | 0.011 | 0.173 | 0.199 | Comparison |

As can be seen from Table 2, all tested electroluminescent devices incorporating a phosphorescent organometallic complex demonstrated increased luminescence efficiency and luminance relative to the comparative device without a phosphorescent organometallic complex, Example 8.

The electroluminescence spectra of devices 3-8 are shown in FIG. 3. As can be seen from FIG. 3, all tested devices incorporating a phosphorescent organometallic material clearly demonstrated shifted color and maximum emission wavelength compared to the comparative devices without a phosphorescent organometallic complex, indicating that energy was transferred efficiently from the host material of the light-emitting layer to the added phosphorescent dopant, then emitting visible light. Further, it can be seen from Table 2 and FIG. 3 that, with the increase of the concentration of the phosphorescent dopant material, the luminescent efficiency did not decrease and there is no indication of the formation of excimers which should emit at a longer wavelength.

The invention has been described in detail with particular reference to certain preferred embodiments thereof, but it will be understood that variations and modifications can be effected within the spirit and scope of the invention. The patents and other publications referred to herein are hereby incorporated by reference.

PARTS LIST

101 Substrate
103 Anode
105 Hole Injecting layer (HIL)
107 Hole Transporting layer (HTL)
108 Exciton blocking layer (EBL)
109 Light Emitting layer (LEL)
110 Hole and/or Excition Blocking layer (HBL)
111 Electron Transporting layer (ETL)
113 Cathode
150 Voltage/Current Source
160 Conductors

The invention claimed is:

1. An electroluminescent device comprising a light-emitting layer containing a light emitting material that contains an organometallic complex is represented by formula (II)

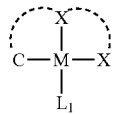

(II)

wherein,
M represents a metal selected from group 10 metals;
C represents a carbon atom;
X represents a heteroatom selected from N or O in which one X forms a covalent bond with the metal and the other X forms a coordinative bond with the metal; and
$L_1$ represents a phosphine ligand that coordinates to the metal through a coordinative bond.

2. The organometallic complex of claim 1 wherein the ligand $L_1$ is selected from the following compounds:

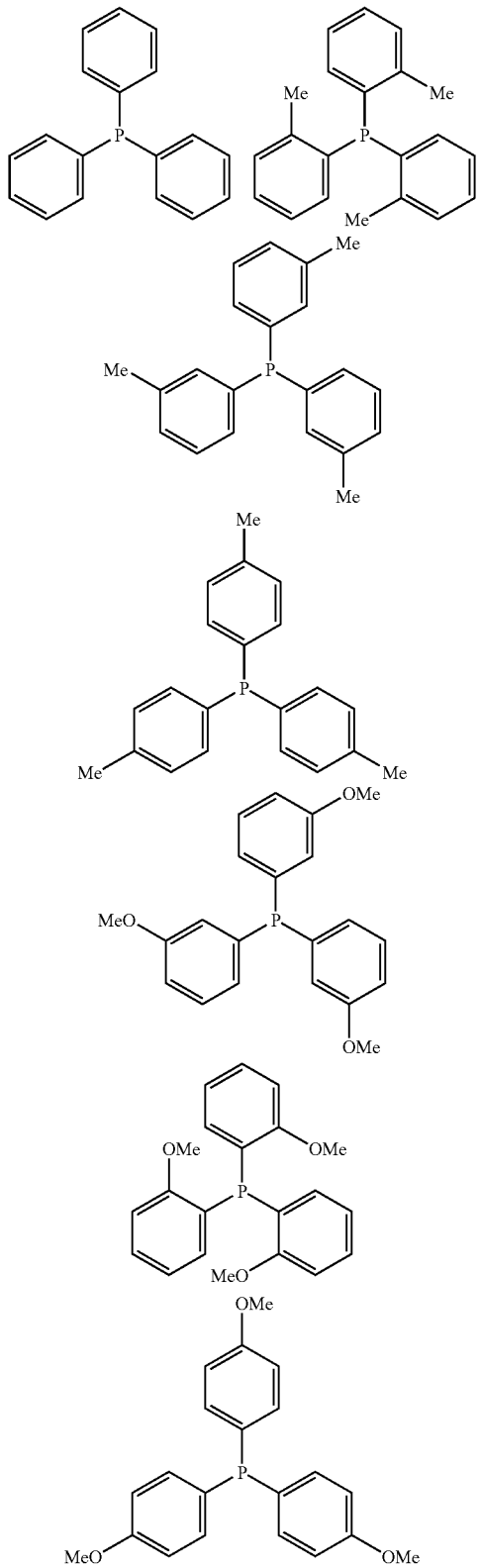

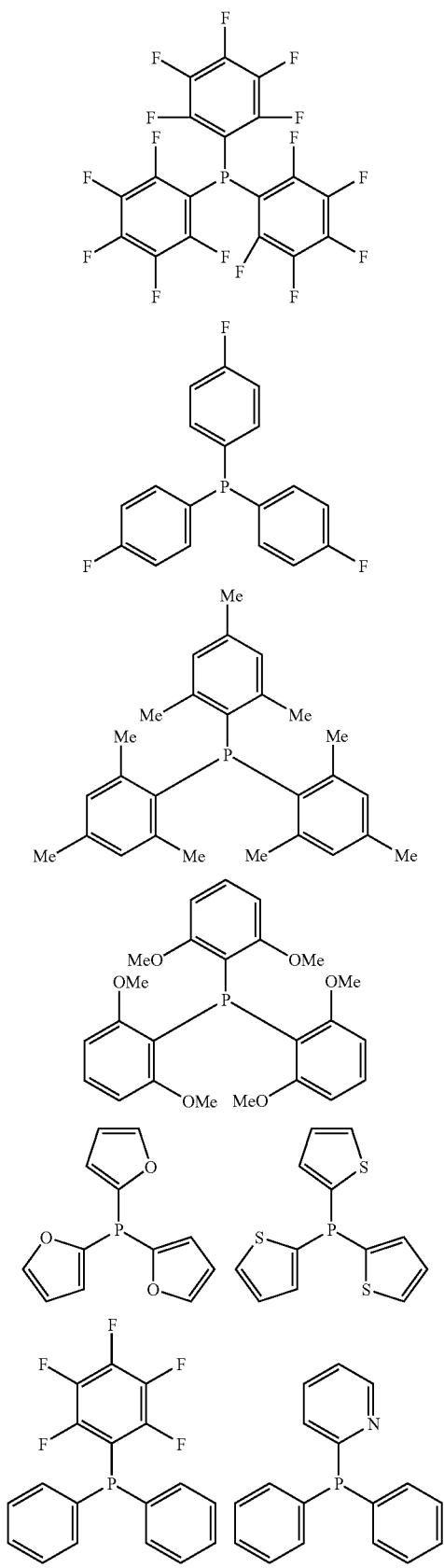

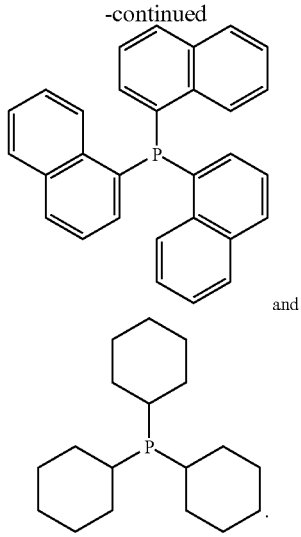

and

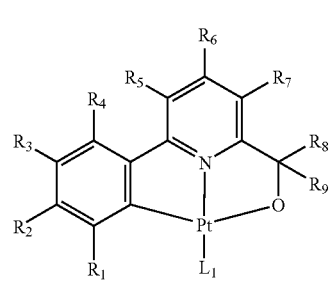

3. An electroluminescence device comprising a light-emitting layer containing a light emitting material that contains an organometallic complex wherein the organometallic complex is represented by the following formula (IX):

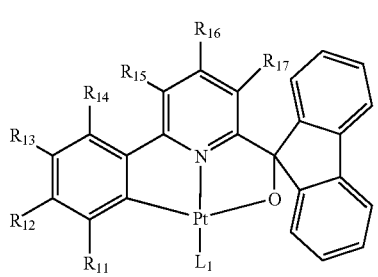

(IX)

wherein
$R^1$-$R^9$ represent hydrogen or independently selected substituent groups, provided that $R^1$ and $R^2$, $R^2$ and $R^3$, $R^3$ and $R^4$, $R^4$ and $R^5$, $R^5$ and $R^6$, $R^6$ and $R^7$, $R^7$ and $R^8$, as well as $R^8$ and $R^9$ may combine to form a ring group; and
$L_1$ represents a ligand that coordinates to the Pt through a coordinative bond.

4. The electroluminescence device of claim 3 wherein the organometallic complex is represented by the formula (X):

(X)

wherein,
$R^{11}$-$R^{17}$ represent hydrogen or independently selected substituent groups, provided that adjacent two groups may combine to form a ring group, as well as $R^{14}$ and $R^{15}$ may combine to form a ring group; and $L_1$ represents a ligand that coordinates to the Pt through a coordinative bond.

5. The device of claim 4 wherein $L_1$ is selected from triarylphosphines represented by $Ar_3P$ wherein each Ar independently represents a substituent selected from aromatic groups or heteroaromatic groups.

6. The electroluminescent device of claim 1 wherein the organometallic complex is a dopant compound dispersed in a host material.

7. The electroluminescent device of claim 6 wherein the dopant compound is present in an amount of up to 15% wt % based on the host.

8. The electroluminescent device of claim 1 that emits white light.

* * * * *